(12) United States Patent
Shum et al.

(10) Patent No.: US 11,814,619 B2
(45) Date of Patent: Nov. 14, 2023

(54) COMPOSITIONS, METHODS, AND SYSTEMS FOR SINGLE CELL BARCODING AND SEQUENCING

(71) Applicant: Enumerix, Inc., Palo Alto, CA (US)

(72) Inventors: Eleen Yee Lam Shum, San Carlos, CA (US); Janice Hoiyi Lai, Mountain View, CA (US); Hei Mun Christina Fan, Palo Alto, CA (US); Stephen P. A. Fodor, Palo Alto, CA (US)

(73) Assignee: ENUMERIX, INC., Palo Alto, CA (US)

( * ) Notice: Subject to any disclaimer, the term of this patent is extended or adjusted under 35 U.S.C. 154(b) by 0 days.

(21) Appl. No.: 17/834,649

(22) Filed: Jun. 7, 2022

(65) Prior Publication Data

US 2022/0389410 A1    Dec. 8, 2022

Related U.S. Application Data

(63) Continuation of application No. PCT/US2022/032097, filed on Jun. 3, 2022.
(Continued)

(51) Int. Cl.
*C12N 1/15* (2006.01)
*C12Q 1/6874* (2018.01)
(Continued)

(52) U.S. Cl.
CPC ....... *C12N 15/1065* (2013.01); *C12Q 1/6806* (2013.01); *C12Q 1/6874* (2013.01)

(58) Field of Classification Search
None
See application file for complete search history.

(56) References Cited

U.S. PATENT DOCUMENTS

| 3,480,616 A | 11/1969 | Osipow, I et al. |
| 3,644,333 A | 2/1972 | Osipow, I et al. |

(Continued)

FOREIGN PATENT DOCUMENTS

| CN | 1089361 A | 7/1994 |
| CN | 2612943 Y | 4/2004 |

(Continued)

OTHER PUBLICATIONS

Macosko et al., "Highly Parallel Genome-wide Expression Profiling of Individual Cells Using Nanoliter Droplets," Cell 2015, 161: 1202-1214. (Year: 2015).*

(Continued)

*Primary Examiner* — Kaijiang Zhang
(74) *Attorney, Agent, or Firm* — Wilson Sonsini Goodrich & Rosati

(57) ABSTRACT

This disclosure provides for devices, methods, and systems for generating a plurality of droplets within a collecting container at an extremely high rate (e.g., of at least 1 million droplets per minute, etc.), the plurality of droplets generated from an aqueous mixture comprising a set of single cells and a set of functionalized particles configured for a single cell assay. Upon generation, the plurality of droplets can be stabilized in position within a region of the collecting container, thereby providing a single-tube workflow for single cell analyses. Further, compositions implemented are structured to allow for overloading of partitions with functionalized particles, such that partitioned single-cells are co-localized with a subset of functionalized particles in a manner that allows for discernable tagging and downstream analyses.

21 Claims, 14 Drawing Sheets

Related U.S. Application Data

(60) Provisional application No. 63/196,815, filed on Jun. 4, 2021.

(51) Int. Cl.
  *C12Q 1/6806* (2018.01)
  *C12N 15/10* (2006.01)

(56) References Cited

U.S. PATENT DOCUMENTS

| | | |
|---|---|---|
| 4,683,058 A | 7/1987 | Lyman et al. |
| 5,051,182 A | 9/1991 | Wang et al. |
| 5,216,033 A | 6/1993 | Pereira et al. |
| 5,707,613 A | 1/1998 | Hill |
| 5,753,241 A | 5/1998 | Ribier et al. |
| 5,925,338 A | 7/1999 | Karassik et al. |
| 6,120,778 A | 9/2000 | Simonnet |
| 6,121,055 A | 9/2000 | Hargreaves |
| 6,379,682 B1 | 4/2002 | Tchinnis et al. |
| 6,387,357 B1 | 5/2002 | Chopra et al. |
| 6,403,069 B1 | 6/2002 | Chopra et al. |
| 7,041,481 B2 | 5/2006 | Anderson et al. |
| 8,871,444 B2 | 10/2014 | Griffiths et al. |
| 8,889,093 B2 | 11/2014 | Malhotra et al. |
| 9,012,390 B2 | 4/2015 | Holtze et al. |
| 9,029,083 B2 | 5/2015 | Griffiths et al. |
| 9,039,273 B2 | 5/2015 | Weitz et al. |
| 9,074,242 B2 | 7/2015 | Larson et al. |
| 9,127,310 B2 | 9/2015 | Larson et al. |
| 9,410,151 B2 | 8/2016 | Link et al. |
| 9,446,360 B2 | 9/2016 | Mazutis |
| 9,470,617 B2 | 10/2016 | Durack |
| 9,562,837 B2 | 2/2017 | Link |
| 9,610,239 B2 | 4/2017 | Feng et al. |
| 9,788,564 B2 | 10/2017 | Bromley |
| 9,901,887 B2 | 2/2018 | Schultz et al. |
| 10,384,961 B2 | 8/2019 | Solomon et al. |
| 10,428,326 B2 | 10/2019 | Belhocine et al. |
| 10,537,503 B2 | 1/2020 | Lei et al. |
| 10,619,192 B2 | 4/2020 | Chiu et al. |
| 10,745,742 B2 | 8/2020 | Bent et al. |
| 11,097,247 B2 | 8/2021 | Lebofsky et al. |
| 11,155,809 B2 | 10/2021 | Lebofsky |
| 11,161,087 B2 | 11/2021 | Fan et al. |
| 11,162,136 B1 | 11/2021 | Fan et al. |
| 11,242,558 B2 | 2/2022 | Fan et al. |
| 11,447,817 B2 | 9/2022 | Fan et al. |
| 11,542,546 B2 | 1/2023 | Fan et al. |
| 2004/0081633 A1 | 4/2004 | Mercier et al. |
| 2006/0128883 A1 | 6/2006 | Garrison et al. |
| 2008/0182910 A1 | 7/2008 | Qiu et al. |
| 2009/0239308 A1 | 9/2009 | Dube et al. |
| 2012/0258516 A1 | 10/2012 | Schultz et al. |
| 2012/0322058 A1 | 12/2012 | Regan et al. |
| 2014/0272996 A1 | 9/2014 | Bemis |
| 2016/0158752 A1 | 6/2016 | Chiou et al. |
| 2018/0092847 A1 | 4/2018 | Schutt et al. |
| 2018/0135117 A1 | 5/2018 | Link |
| 2018/0136114 A1 | 5/2018 | Delattre et al. |
| 2019/0076794 A1 | 3/2019 | Solomon et al. |
| 2019/0255531 A1 | 8/2019 | Hindson et al. |
| 2019/0323088 A1 | 10/2019 | Boutet et al. |
| 2019/0358625 A1 | 11/2019 | Huang et al. |
| 2020/0037638 A1 | 2/2020 | Faraci et al. |
| 2020/0188920 A1 | 6/2020 | Delaney et al. |
| 2021/0349027 A1 | 11/2021 | Fei et al. |
| 2022/0170085 A1 | 6/2022 | Fan et al. |
| 2022/0339620 A1 | 10/2022 | Huang et al. |

FOREIGN PATENT DOCUMENTS

| | | |
|---|---|---|
| CN | 1758405 A | 4/2006 |
| CN | 103145346 A | 6/2013 |
| CN | 103649813 A | 3/2014 |
| CN | 104111242 A | 10/2014 |
| CN | 104237186 A | 12/2014 |
| CN | 104284970 A | 1/2015 |
| CN | 104407436 A | 3/2015 |
| CN | 104741156 A | 7/2015 |
| CN | 104741158 A | 7/2015 |
| CN | 104815709 A | 8/2015 |
| CN | 105854965 A | 8/2016 |
| CN | 106053346 A | 10/2016 |
| CN | 106076443 A | 11/2016 |
| CN | 207062288 U | 3/2018 |
| CN | 109060736 A | 12/2018 |
| JP | 3568846 B2 | 9/2004 |
| WO | WO-2008079274 A1 | 7/2008 |
| WO | WO-2009149449 A1 | 12/2009 |
| WO | WO-2015097185 A1 | 7/2015 |
| WO | WO-2015164212 A1 | 10/2015 |
| WO | WO-2017215428 A1 | 12/2017 |
| WO | WO-2017215429 A1 | 12/2017 |
| WO | WO-2020001529 A1 | 1/2020 |

OTHER PUBLICATIONS

Chen et al., "Centrifugal micro-channel array droplet generation for highly parallel digital PCR," Lab Chip 2017, 17:235-240. (Year: 2017).*

Abate et al.: Faster multiple mulsification with drop splitting. Lab on a Chip vol. 11 (2011).

Liao et al.: Combination of fluorescence color and melting temperature as a two-dimensional label for homogeneous multiplex PCR detection. Nucleic Acids Research 2013, 41:7 e76 (2013).

McMahon et al.: Multiplexed Single Intact Cell Droplet Digital PCR (MuSIC ddPCR) Method for Specific Detection of Enterohemorrhagic E. coli (EHEC) in Food Enrichment Cultures. Frontiers in Microbiology 8:332 (2017).

PCT/CN2017/085891 International Search Report and Written Opinion dated Sep. 1, 2017.

PCT/CN2017/085892 International Search Report and Written Opinion dated Aug. 11, 2017.

PCT/CN2019/093241 International Search Report and Written Opinion dated Oct. 8, 2019.

PCT/CN2019/093241 International Search Report and Written Opinion dated Aug. 10, 2019.

PCT/US2021/027353 International Search Report and Written Opinion dated Aug. 13, 2021.

PCT/US2022/032097 International Search Report and Written Opinion dated Oct. 19, 2022.

Schulman et al.: Formation of microemulsions by amino alkyl alcohols. Ann N Y Acad Sci. 92:366-371 doi:10.1111/j.1749-6632.1961.tb44987.x (1961).

Vladisavljevicć et al.: Production of uniform droplets using membrane, microchannel and microfluidic emulsification devices. Microfluidics and Nanofluidics 13:151-178 (2012).

Wright et al.: The use of cell-free fetal nucleic acids in maternal blood for non-invasive prenatal diagnosis. Human Reproduction Update 15(1):139-151 (2009).

Yamashita et al.: Generation of monodisperse cell-sized microdroplets using a centrifuge-based axisymmetric co-flowing microfluidic device. Journal of Bioscience and Bioengineering 119(4): 492-495 (2014).

Yanny et al.: Miniscope3D: optimized single-shot miniature 3D fluorescence microscopy. Light: Science & Applications 9:171 (2020).

Zhao et al.: Massive droplet generation for digital PCR via a smart step emulsification chip integrated in a reaction tub. Analyst 2021, 146:15568 (2021).

Zhu et al.: Highly sensitive and quantitative detection of rare pathogens through agarose droplet microfluidic emulsion PCR at the single-cell level. Lab On a Chip 12(20):3907-3913 (2012).

* cited by examiner

Method 300

400 providing a set of particles distributed across a set of partitions, wherein a subset of partitions of the set of partitions contain target material from isolated single cells S410

For each partition: promoting selective capture of the target material by the first subset of molecules coupled to the subset of particles within the partition S420

For each partition: triggering release of the second subset of molecules for interactions with the third subset of molecules of other particles within the partition S430

For each partition: generating a set of amplifiable templates with linked barcode segments associated with the subset of particles within the partition, as a bead-linked library for sequencing S440 sequencing the set of amplifiable templates after combining material from the set of partitions S450 generating a network of linked barcodes from the set of amplifiable templates upon performing a set of operations S460 from the network of linked barcodes, determining a set of particle characteristics for each partition S470 from the set of particle characteristics, generating a single cell expression library from sequenced analytes associated with the set of particle characteristics for each partition S480

FIG. 4B

COMPOSITIONS, METHODS, AND SYSTEMS FOR SINGLE CELL BARCODING AND SEQUENCING

CROSS-REFERENCE

This application is a continuation application of PCT Patent Application number PCT/US2022/032097, filed Jun. 3, 2022, which claims the benefit of U.S. Provisional Application No. 63/196,815, filed Jun. 4, 2021, each of which is incorporated in its entirety herein by this reference.

TECHNICAL FIELD

This disclosure relates generally to fields related to sample processing and sequencing, and more specifically to new and useful systems, methods, and compositions for single cell and/or other target characterization in such fields.

BACKGROUND OF THE INVENTION

Cells have been traditionally studied at the cell population level or tissue level until recently, with developments in technologies for characterization of cells at single-cell resolution. Genomic, transcriptomic, or other multi-omic characterization of cells at single-cell resolution has many applications in understanding pathological conditions, characterizing disease progression, immune response, performing explorational studies (e.g., in organism development), and addressing other biological problems. However, current methods for sequencing at single-cell resolution are subject to low capture efficiency and/or involve specialized devices (e.g., microfluidic devices), which often result in increased workflow times, reduced accuracy, and/or increased run costs.

SUMMARY OF THE INVENTION

Currently, methods and systems for single cell analysis involving partitions involve highly complex setups, with precise control of single-cell sample distribution and functionalized particle distribution across partitions. Most methods involve encapsulation of single cells with barcoded processing materials (e.g., olignonucleotides, primers, etc.) within the same partition, such that all nucleic acid molecules from a single cell are tagged with the same barcode sequence, and such that the molecules from each cell can be associated to the same single cell after sequencing or other post-processing operations. For high-throughput single cell assays, each single cell is co-localized with many barcoding molecules (either via priming or ligation) containing the same cell barcode sequence. The barcoding molecules are often delivered to each cell by a single physical particle/bead, and having multiple beads/barcodes associated with a single partition and cell is not desirable. As such, single cell analysis platforms typically aim to co-capture cells and functionalized particles within partitions in a 1:1 manner, or to underload functionalized particles such that partitions each only have 0 or 1 functionalized particle.

Accordingly, this disclosure describes embodiments, variations, and examples of systems, methods, and compositions for breaking requirements around single cell sample processing in a highly-efficient manner and with less complexity of sample and particle distribution setups.

An aspect of the disclosure provides embodiments, variations, and examples of devices, methods, and compositions that remove requirements for providing a single or less than one functionalized particle for barcoding single cell material (e.g., where such requirements are typically associated with technologies involving fluidic devices and/or specialized particle structures). In particular, the disclosure provides systems and methods for barcoding of single cell material that function with more than one functionalized particle provided per single cell/partition.

Relatedly, an aspect of the disclosure provides embodiments, variations, and examples of devices and methods for rapidly generating partitions (e.g., droplets from a sample fluid, droplets of an emulsion) and distributing single cells and functionalized particles across partitions, wherein, the device includes: a first substrate defining a reservoir comprising a reservoir inlet and a reservoir outlet; a membrane coupled to the reservoir outlet and comprising a distribution of holes; and a supporting body comprising an opening configured to retain a collecting container in alignment with the reservoir outlet. During operation, the first substrate can be coupled with the supporting body and enclose the collecting container, with the reservoir outlet aligned with and/or seated within the collecting container. During operation, the reservoir can contain a sample fluid (e.g., a mixture of single cells and functionalized molecules/particles), where application of a force to the device or sample fluid generates a plurality of droplets within the collecting container at an extremely high rate (e.g., of at least 10,000 droplets/minute, of at least 20,000 droplets/minute, of at least 30,000 droplets/minute, of at least 40,000 droplets/minute, of at least 50,000 droplets/minute, of at least 100,000 droplets/minute, 200,000 droplets/minute, of at least 300,000 droplets/minute, of at least 400, droplets/minute, of at least 500,000 droplets/minute, of at least 600,000 droplets/minute, of at least 700,000 droplets/minute, of at least 800,000 droplets/minute, of at least 900,000 droplets/minute, of at least 1 million droplets/minute, of at least 2 million droplets/minute, of at least 3 million droplets/minute, etc.), where the droplets are stabilized in position (e.g., in a close-packed format, in equilibrium stationary positions) within the collecting container. Notably, the droplets are stable across a wide range of temperatures (e.g., 1° C. through 95° C., greater than 95° C., less than 1° C.) relevant to various digital analyses and other bioassays, where the droplets remain consistent in morphology and remain unmerged with adjacent droplets. Furthermore, such systems and methods partition single cells and functionalized particles (with more than one functionalized particle per partition) in an extremely rapid and efficient manner.

An aspect of the disclosure provides embodiments, variations, and examples of a method for rapidly generating partitions (e.g., droplets from a sample fluid, droplets of an emulsion) within a collecting container at an extremely high rate, each of the plurality of droplets including an aqueous mixture for a digital analysis (e.g., of single cells, of nucleic acid material, of protein material, of amino acid material, of other analytes described), wherein upon generation, the plurality of droplets is stabilized in position (e.g., in a close-packed format, at equilibrium stationary positions, etc.) within a continuous phase (e.g., as an emulsion having a bulk morphology defined by the collecting container). In aspects, partition generation can be executed by driving the sample fluid through a distribution of holes of a membrane, where the applied force can be one or more of centrifugal (e.g., under centrifugal force), associated with applied pressure, magnetic, or otherwise physically applied.

In relation to a single-tube workflow in which the collecting container remains closed (e.g., the collecting container has no outlet, there is no flow out of the collecting container, to avoid sample contamination), method(s) can further include transmitting heat to and from the plurality of droplets within the closed collecting container according to an assay protocol. In relation to generation of emulsions having suitable clarity (e.g., with or without refractive index matching), method(s) can further include transmission of signals from individual droplets from within the closed collecting container, for readout (e.g., by an optical detection platform, by another suitable detection platform).

Where method(s) include transmitting heat to and from the plurality of droplets, within the closed container, the droplets are stable across a wide range of temperatures (e.g., 1° C. through 95° C., greater than 95° C., less than 1° C.) relevant to various digital analyses and other bioassays, where the droplets remain consistent in morphology and remain unmerged with adjacent droplets.

Examples of partition generation methods can include generating an extremely high number of droplets (e.g., greater than 1 million droplets, greater than 2 million droplets, greater than 3 million droplets, greater than 4 million droplets, greater than 5 million droplets, greater than 6 million droplets, greater than 7 million droplets, greater than 8 million droplets, greater than 9 million droplets, greater than 10 million droplets, greater than 15 million droplets, greater than 20 million droplets, greater than 25 million droplets, greater than 30 million droplets, greater than 40 million droplets, greater than 50 million droplets, greater than 100 million droplets, etc.) within a collecting container having a volumetric capacity (e.g., less than 50 microliters, from 50 through 100 microliters and greater, etc.), where droplets have a characteristic dimension (e.g., from 1-50 micrometers, from 10-30 micrometers, etc.) that is relevant for digital analyses, single cell capture, target detection, individual molecule partitioning, or other applications.

Relatedly, an aspect of the disclosure provides embodiments, variations, and examples of non-naturally occurring compositions for facilitating isolation of single cells, amplification of nucleic acid material from isolated individual cells, constructing sequencing libraries, and sequencing nucleic acid material for characterization of single cells. The disclosure provides compositions, methods, and systems for enabling performance of single-cell analyses, with vastly improved capture efficiency, without utilizing complex microfluidic setups, and in a manner that reduces overall costs. However, aspects of the disclosure can alternatively be utilized in coordination with various technologies for isolating cells in single-cell format (e.g., by use of wells, by use of droplets, by use of other partitioning elements, etc.).

An aspect of the disclosure provides embodiments, variations, and examples of methods for linking functionalized particles or linking molecules of functionalized particles within a partition, where the functionalized particles include molecular sequences that can be used for barcoding of cellular material captured in the partition, and molecular sequences that can be released/cleaved in order to hybridize with complementary sequences of other functionalized molecules in the partition, thereby linking functionalized particles in the partition.

Aspects of the disclosure further provide embodiments, variations, and examples of functionalized particles that link with corresponding functionalized particles in a partition, while preventing self-hybridization.

An aspect of the disclosure provides embodiments, variations, and examples of compositions including a set of partitions, where some of the partitions contain multiple functionalized particles without an associated captured single cell (or single cell-derived material, single particles, single nuclei, etc.), and where some/most of (e.g., at least 90% of, other suitable percentages of) the partitions contain at least one functionalized particle with an associated captured single cell (or single cell-derived material), thereby "super-loading" functionalized particles with isolated single cells in a greater than 1:1 ratio between functionalized particles and isolated single cells (or single cell-derived material).

In embodiments, the methods, systems, devices, and compositions disclosed herein can optimize the number of functionalized particles needed per partition (e.g., based upon Poisson distribution aspects), as well as density of functionalized particles needed to provide a unique barcode library for each isolated individual cell.

Aspects of the disclosure further provide embodiments, variations, and examples of methods and systems for efficient capture and labeling of target material (e.g., DNA, RNA, miRNA, proteins, small molecules, single analytes, multianalytes, etc.) in order to enable genomic, proteomic, and/or other multi-omic characterization of single cells for various applications. For nucleic acid targets, capture probes of compositions described can include complementary molecules to the nucleic acid targets. For protein targets or small molecule targets, capture probes of the compositions described can include antibodies or aptamers conjugated with specific nucleic acid sequences for detection.

Aspects of the disclosure also confer(s) the benefit of enabling applications in spatial transcriptomics. For instance, compositions, methods, and systems described can be used for mapping of targets in a sample over time, in order to understand disease pathology and progression (e.g., spread of targets and changes in expression over time).

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. The present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entireties for all purposes and to the same extent as if each individual publication, patent, or patent application was specifically and individually indicated to be incorporated by reference.

Furthermore, where a range of values is provided, it is understood that each intervening value, between the upper and lower limit of that range and any other stated or intervening value in that stated range is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either both of those included limits are also included in the disclosure.

BRIEF DESCRIPTION OF THE DRAWINGS

FIG. 4B depicts an embodiment of a method for single cell barcoding and sequencing.

DETAILED DESCRIPTION OF THE INVENTION(S)

Figure 1A:
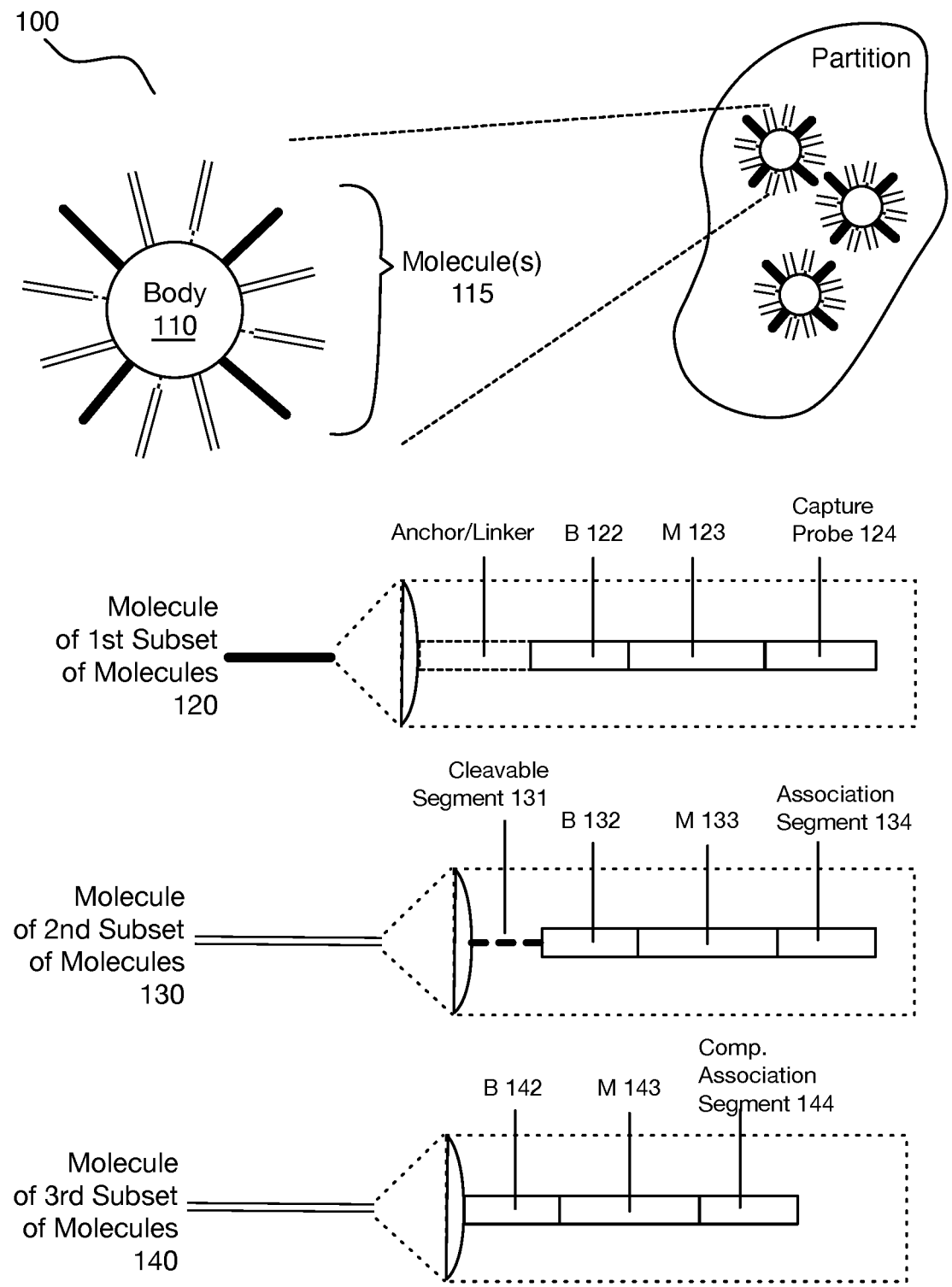
FIG. 1A depicts a schematic of an embodiment of a composition for single cell barcoding and sequencing.

While various embodiments of the invention have been shown and described herein, it will be obvious to those skilled in the art that such embodiments are provided by way of example only. Numerous variations, changes, and substitutions can occur to those skilled in the art without departing from the invention. It should be understood that various alternatives to the embodiments of the invention described herein can be employed.

1. General Overview

The present disclosure covers systems, devices, methods performed by such systems and devices, and compositions supporting such methods, in relation to single cell partitioning and analyses. Generally, embodiments of the device include assemblies of reservoirs, functionalized membranes/plates, and supporting bodies for collecting containers, where the assemblies rapidly produce droplets of an emulsion for single cell partitioning or other applications of use. Droplets produced by such devices are stabilized in a three-dimensional format within closed collecting containers, thereby providing a "single-tube" workflow that eliminates risk of sample cross-contamination from initial reception of a sample, to distributing of the sample across an extremely high number of partitions, to performance of reactions within individual partitions, to detecting signals generated by contents of individual partitions from with the closed collecting containers.

The systems, methods, and devices disclosed herein can provide several additional benefits over other systems and methods, and such systems, methods, and devices are further implemented into many practical applications across various disciplines.

Devices, methods, systems, and compositions of the present disclosure may generate a plurality of droplets at an extremely high rate, where the droplets are stabilized in position (e.g., in a close-packed format, in equilibrium stationary positions) within a collecting container. Notably, the droplets are stable across a wide range of temperatures (e.g., 1° C. through 95° C., greater than 95° C., less than 1° C.) relevant to various single cell and digital analyses and other bioassays, where the droplets remain consistent in morphology and remain unmerged with adjacent droplets. Stabilization of the droplets within a continuous phase of an emulsion is further performed in a manner where the emulsion has a high degree of clarity (e.g., greater than 50% transmissivity of light, greater than 60% transmissivity of light, greater than 70% transmissivity of light, greater than 80% transmissivity of light, greater than 90% transmissivity of light, greater than 99% transmissivity of light, etc.), such that signals from cross-sections of the emulsion within the collecting container can be interrogated (e.g., using a 3D imaging technique, using a planar imaging technique, etc.).

The devices, systems, methods, and compositions disclosed herein can further remove requirements for providing a single or less than one functionalized particle for barcoding single cell material (associated with technologies involving fluidic devices and/or specialized particle structures). In particular, the disclosure provides systems and methods for barcoding of single cell material that function with more than one functionalized particle provided per single cell/partition.

Relatedly, the devices, systems, and methods disclosed herein can further rapidly generate partitions (e.g., droplets from a sample fluid, droplets of an emulsion) and distribute single cells and functionalized particles across partitions, wherein, the device includes: a first substrate defining a reservoir comprising a reservoir inlet and a reservoir outlet; a membrane coupled to the reservoir outlet and comprising a distribution of holes; and a supporting body comprising an opening configured to retain a collecting container in alignment with the reservoir outlet. During operation, the first substrate can be coupled with the supporting body and enclose the collecting container, with the reservoir outlet aligned with and/or seated within the collecting container. During operation, the reservoir can contain a sample fluid (e.g., a mixture of single cells and functionalized molecules/particles), where application of a force to the device or sample fluid generates a plurality of droplets within the collecting container at an extremely high rate (e.g., of at least 10,000 droplets/minute, of at least 20,000 droplets/minute, of at least 30,000 droplets/minute, of at least 40,000 droplets/minute, of at least 50,000 droplets/minute, of at least 100,000 droplets/minute, of at least 200,000 droplets/minute, of at least 300,000 droplets/minute, of at least 400, droplets/minute, of at least 500,000 droplets/minute, of at least 600,000 droplets/minute, of at least 700,000 droplets/minute, of at least 800,000 droplets/minute, of at least 900,000 droplets/minute, of at least 1 million droplets/minute, of at least 2 million droplets/minute, of at least 3 million droplets/minute, etc.), where the droplets are stabilized in position (e.g., in a close-packed format, in equilibrium stationary positions) within the collecting container. Notably, the droplets are stable across a wide range of temperatures (e.g., 1° C. through 95° C., greater than 95° C., less than 1° C.) relevant to various digital analyses and other bioassays, where the droplets remain consistent in morphology and remain unmerged with adjacent droplets. Furthermore, such systems and methods partition single cells and functionalized particles (with more than one functionalized particle per partition) in an extremely rapid and efficient manner.

Cellular material processed by the systems, methods, and devices described can include one or more of: stem cells, cancer cells, blood cells, peripheral blood mononuclear cells, other immune cells, circulating tumor cells, breast cancer cells, cells or cellular material from any suitable tissue source, cells at a cell cycle phase of desire, plant cells or cellular material, fungal cells or cellular material, vesicles (e.g., synthetically-derived vesicles), pathogens, bacteria, viruses, viral vectors, subcellular particles, and/or other types of cells, cellular material, and objects having similar morphology and/or characteristics to cells.

Compositions described herein can facilitate isolation and unique identification of single cells, amplification of nucleic acid material from isolated individual cells, construction of sequencing libraries, and sequencing of nucleic acid material for characterization of single cells. The disclosure can provide compositions, methods, and systems for enabling performance of single-cell analyses, with vastly improved capture efficiency, without utilizing complex microfluidic setups, and in a manner that reduces overall costs.

However, the aspects of the disclosure can be utilized in coordination with various technologies for isolating cells in single-cell format (e.g., by use of wells, by use of droplets, by use of other partitioning elements, etc.).

Described herein are methods and compositions for linking functionalized particles within a partition, where the functionalized particles include molecular sequences that can be used for barcoding of cellular material captured in the partition, and molecular sequences that can be released/cleaved in order to hybridize with complementary sequences of other functionalized molecules in the partition, thereby linking functionalized particles in the partition.

Disclosed herein are compositions that can include functionalized particles that thus link with corresponding functionalized particles in a partition, while preventing self-hybridization.

Further disclosed herein are compositions including a set of partitions, where some of the partitions contain multiple functionalized particles without an associated captured single cell (or single cell-derived material, single particles, single nuclei, etc.), and where some/most of (e.g., at least 90% of, other suitable percentages of) the partitions contain at least one functionalized particle with an associated captured single cell (or single cell-derived material), thereby "super-loading" functionalized particles with isolated single cells in a greater than 1:1 ratio between functionalized particles and isolated single cells (or single cell-derived material).

Methods, systems, devices, and compositions as disclosed herein can optimize the number of functionalized particles needed per partition (e.g., based upon Poisson distribution aspects), as well as density of functionalized particles needed to provide a unique barcode library for each isolated individual cell.

The devices, systems, methods, and compositions disclosed herein can further provide mechanisms for efficient capture and labeling of target material (e.g., DNA, RNA, miRNA, proteins, small molecules, single analytes, multi-analytes, etc.) in order to enable genomic, proteomic, and/or other multi-omic characterization of single cells for various applications. For nucleic acid targets, capture probes of compositions described can include complementary molecules to the nucleic acid targets. For protein targets or small molecule targets, capture probes of the compositions described can include antibodies or aptamers conjugated with specific nucleic acid sequences for detection.

The devices, systems, methods, and compositions disclosed herein can further enable applications in spatial transcriptomics. For instance, compositions, methods, and systems described can be used for mapping of targets in a sample over time, in order to understand disease pathology and progression (e.g., spread of targets and changes in expression over time).

Additionally or alternatively, the methods, systems, devices, and compositions disclosed herein can confer any other suitable benefit.

2. Particle Composition

FIG. 1A shows an example composition 100 for single cell sequencing include: a body 110, and a set of molecules 115 coupled to the body 110 and structured for functionalization of the composition 100.

Figure 1B:
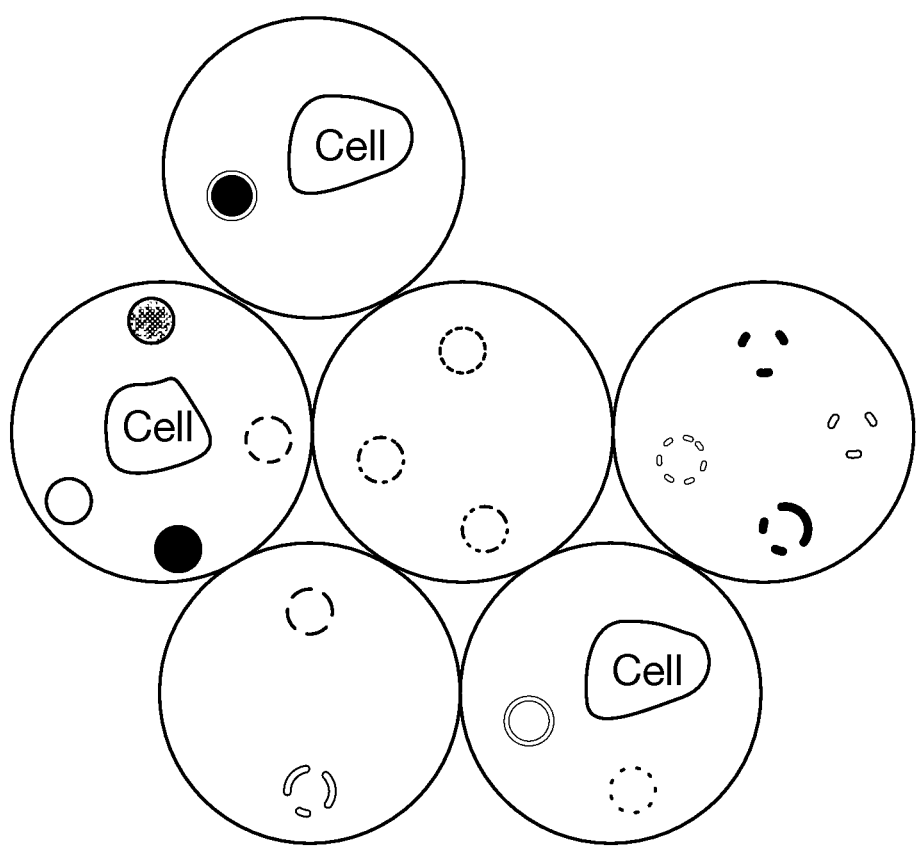
FIG. 1B depicts a schematic of a set of partitions containing a distribution of functionalized particles and single cells.

The composition 100 functions to, along with other variations of the composition 100 isolated with material from a single cell within a partition, tag all nucleic acid molecules from the single cell with a barcode sequence that can be used to uniquely associate the nucleic acid molecules with the respective single cell after sequencing. In particular, the composition 100 is configured to be used in a manner in which single cells are partitioned in a non-high-occupancy regime (e.g., with less than 20% of partitions containing single cells, with less than 19% of partitions containing single cells, with less than 18% of partitions containing single cells, with less than 17% of partitions containing single cells, with less than 16% of partitions containing single cells, with less than 15% of partitions containing single cells, with less than 10% of partitions containing single cells, with 5-10% of partitions containing single cells, with less than 5% of partitions containing single cells, with another suitable percentage of partitions containing single cells), represented in FIG. 1B, but with multiple variations of the composition 100 contained in each partition, thereby "super-loading" the composition 100 with isolated single cells in a greater than 1:1 ratio between functionalized particles and isolated single cells (or single cell-derived material). Thus, a set of single cells of a sample can have a first number, and the set of functionalized particles can have a second number greater than the first number, such that the set of functionalized particles is distributed across partitions with overloading of particles within individual partitions.

As such, the composition 100 can be used to provide a mechanism for high capture efficiency of target material (e.g., all nucleic acid material associated with a single cell), without complex system setups.

Figure 1C:
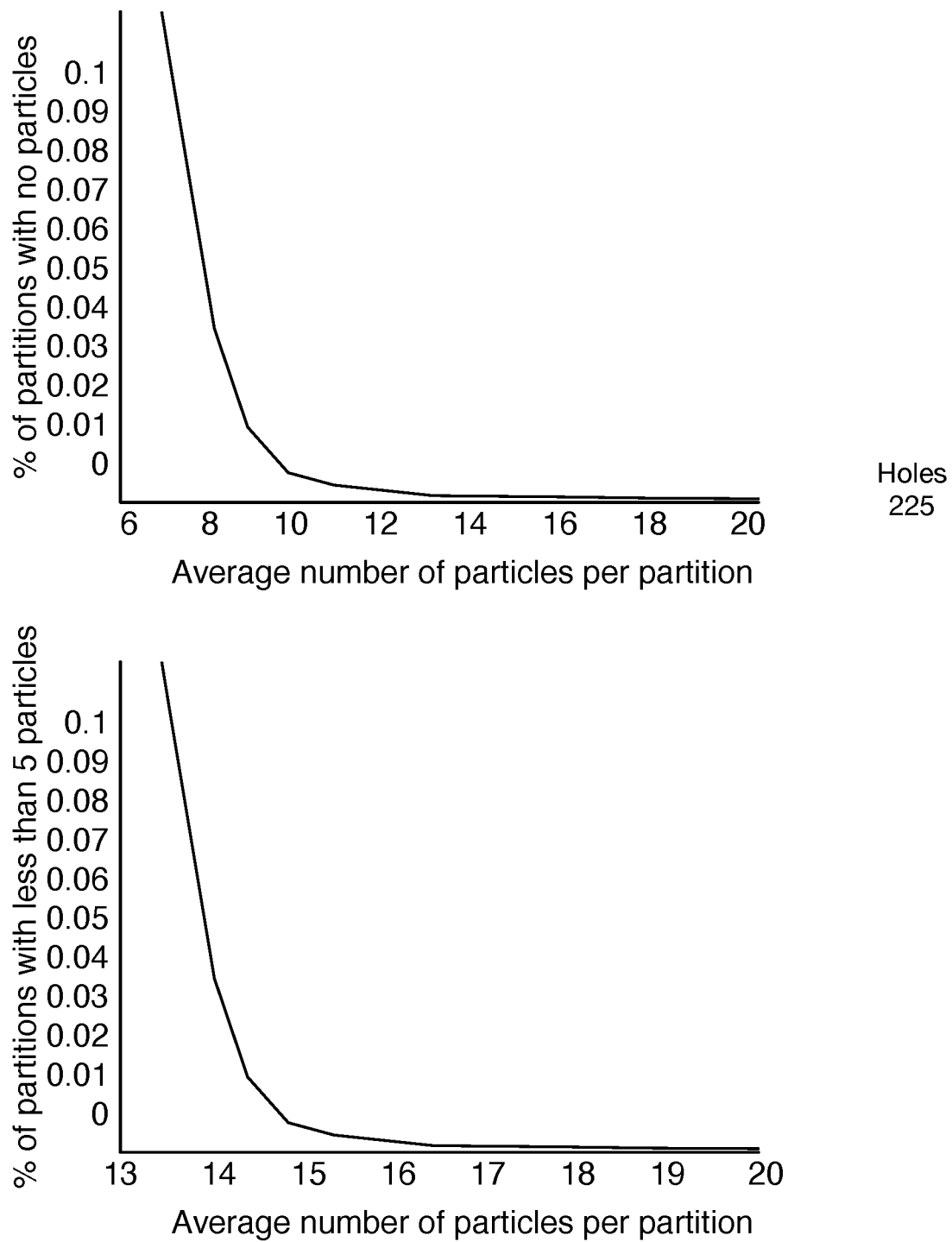
FIG. 1C depicts an example model output relating percentages of partitions with functionalized particles to average number of particles per partition.

In some cases, the number of particles needed per partition can be based upon Poisson distribution factors, where, as shown in FIG. 1C, modeling a relationship between percentage of partitions without any particles against average number of particles per partition according to Poisson distribution factors, produces a requirement of at least 10 particles per partition (average) in order for 99% of partitions to have one particle. With the additional constraint of having at least 5 particles per partition, the modeled relationship produces a requirement of at least 14 particles per partition (average) in order for 99.9% of the partitions to have at least 5 particles.

In some cases described in further detail below, the composition 100 includes a subset of functionalized molecules that can be cleaved from a base substrate (e.g., body 110), where the subset of functionalized molecules can be released from the base substrate (e.g., body 110) and hybridize with complementary molecules of other variations of the composition in the same partition, thereby effectively providing a mechanism by which the compositions in a partition can be associated with each other (e.g., "linked"), and with captured target material. In embodiments, the partitions can include one or more of: droplets (e.g., of an emulsion), wells (e.g., microfluidic wells, nanofluidic wells), or other forms of physical partitioning of cells, sub-cellular structures (e.g., organelles), oligonucleotides, other individual targets, or other analytes.

As such, in some cases (such as that shown in FIG. 1A), the set of molecules 115 can include a first subset of molecules 120 coupled to a body 110 and configured for target analyte capture, where a unit of the first subset 120 can include one or more of: a barcode segment (B) 122, a unique molecule identifier (M) 123, and a capture portion (e.g., probe) 124. In some cases, the set of molecules 115 can include a second subset of molecules 130 configured to be released from the body 110, where a unit of the second subset 130 includes a cleavable segment 131 configured to release the second subset from the body 110 in a controlled manner, the barcode segment (B) 132, the unique molecule identifier (M) 133, and an association segment 134. In some cases, the set of molecules 115 can include a third subset of molecules 140 coupled to the body 110, where a unit of the third subset 130 includes, the barcode segment (B) 142, the unique molecule identifier (M) 143, and a complementary association segment 144 configured to hybridize (e.g., preferentially hybridize) with the association segment 134 of a unit of the second subset of molecules 130 (i.e., of other functionalized particles of the set of functionalized particles within a partition), when the second subset 130 is released from the body 110. In applications, the composition 100 can be provided as a set of particles (e.g., in solution), wherein each of the set of particles is coupled to molecules for various single cell assays. As described in variations below, the association segment 134 and complementary association segment 144 can be configured such that molecules do not self-hybridize in an undesired manner.

The composition 100 can be configured for processes and reactions associated with target capture from a single cell, including one or more of: reverse transcription reactions (RT-reactions) for cDNA synthesis associated with target capture, amplification reactions (e.g., PCR) for amplification of cDNA, high throughput sequencing, ligation, hybridization, polymerase extension, and other suitable reactions.

The composition 100 can be utilized as described in Section 3 below, and/or can be utilized in accordance with other suitable methods.

2.1 Particle—Body

The body 110 functions to provide a substrate to which the set of molecules 115 can be coupled, in order to provide functionalization for the composition 100 with respect to implementation of respective assays and reactions, and association of all particles and captured analytes in a partition.

In relation to morphology, the body 110 can have the form of a microsphere. Alternatively, the body 110 can have the form of a non-spherical (e.g., ellipsoidal, prismatic, polyhedral, amorphous, etc.) body, where a cross section taken through the body 110 is non-circular. However, the body 110 can alternatively have another suitable form. In relation to dimensions, the body 110 can have a diameter (or characteristic width) on the order of nanometers to micrometers in dimension. In particular, the size of the body can be tuned in relation to an intended number of particles per partition (e.g., based upon Poisson distribution characteristics) and a characteristic size of the partition. In variations, the body 110 can have a diameter from 0.04 micrometers to 35 micrometers (e.g., a diameter of 10 micrometers), within a partition having a characteristic dimension from 20-350 micrometers. The body 110 can alternatively have other suitable characteristic dimensions. During use, a solution of the particles can have uniform (or approximately uniform) particle sizes; alternatively, during use, a solution of the particles can have non-uniform particle sizes.

In relation to density, the body 110 can be configured to have a density greater than the density of process liquids intended for use with the composition 100 (e.g., in relation to specific reactions or assays), such that the composition 100 settles within the process liquid(s) by gravity during operation. Alternatively, the body 110 can be configured to have a density equal to the density of process liquids intended for use with the composition 100 (e.g., in relation to specific reactions or assays), such that the composition 100 sits in equilibrium within the process liquid(s) during operation. Still alternatively, the body 110 can be configured to have a density less than the density of process liquids intended for use with the composition 100 (e.g., in relation to specific reactions or assays), such that the composition 100 is buoyant within the process liquid(s) during operation.

In relation to thermal properties, the body 110 is configured to operate between a lower temperature limit (e.g., associated with low temperature reactions and processes, associated with storage, etc.) and an upper temperature limit (e.g., associated with high temperature reactions and processes, such as for thermocycling). However, the body 110 can be configured for other operating temperatures.

In relation to physical properties, the body 110 is configured to maintain structure in solution (e.g., in buffer during storage, in solution during performance of an assay). As such, the body 110 is configured to be non-swelling and non-leaching. However, in alternative embodiments, the body 110 can be configured to swell a desired amount (e.g., in relation to achieving a desired size or morphology for processing or use in an application), configured to leach certain compounds (e.g., process reagents) for performance of an assay, and/or to dissolve in a desired manner during performance of an assay or other process. Further in relation to physical properties, the body 110 can be configured with a desired degree of hydrophilicity (e.g., on a spectrum from hydrophilic to hydrophobic) in relation to performance of an assay or other process. Variations of the body 110 can thus have a suitable type of crosslinking (e.g., chemical crosslinking, physical crosslinking, etc.) and percentage of crosslinking (e.g., from 30-99% crosslinking), to provide a desired level of stability or degradability in conditions of use.

In relation to other surface properties, the body 110 can be configured with a desired density of binding sites, in order to enable achievement of a suitable density of functionalized molecules (e.g., by providing points of attachment on the body 110). Furthermore, the body 110 can include surface groups (e.g., hydroxyl groups, amine groups, carboxyl groups, sulfide groups, silanol groups, etc.) for coupling of molecules described sections below.

In relation to magnetic properties, the body 110 can be configured to respond to magnetic fields (e.g., in relation to assays involving retention of particles in position for subsequent mapping of target analytes from a sample). Certain regions (e.g., a core region) of the body 110 can be magnetic (e.g., magnetic, paramagnetic, etc.), and certain regions (e.g., a shell region) of the body 110 can be non-magnetic in variations of the body 110. In relation to surface properties, the body 110 can be configured with or without charge, in order to facilitate binding to target material of a sample, or to facilitate fabrication involving molecules with functionality, in relation to electroporation applications.

In relation to optical properties, the body 110 can be configured to be non-fluorescent (e.g., so as to not interfere with optical-based detection assays). However, in variations, the body 110 can be configured to be optically detectable (e.g., via a non-fluorescent modality, via a fluorescent modality, via an infrared detection modality, via a thermal detection modality, etc.), for instance, for tracking purposes.

In relation to mechanical properties, the body 110 can be configured to have a desired hardness (e.g., measured on the Mohs scale, measured on another hardness scale), in order to retain a desired level of hardness during applications of use. Additionally or alternatively, the body 110 can be configured with desired mechanical properties associated with one or more of: rigidity, elastic behavior (e.g., in terms of moduli, in terms of plastic and elastic deformation, etc.), viscoelastic behavior, fatigue resistance, fracture resistance, shear strength, compressive strength, tensile strength, rheological behavior (e.g., under conditions of wear), and other mechanical properties.

In relation to composition, the body 110 can be composed of one or more of: polymers (e.g. polystyrene, polystyrene-divinylbenzene, polymethylmethacrylate (PMMA), polyethylene glycol (PEG), etc.), hydrogels, silica, silicon, non-porous glass, porous glass, coated glass, agarose, acrylamide, polyacrylamide, iron, steel, or ceramic materials and/or a combination of one or more suitable materials. As noted above and below, different regions of the body 110 can be composed of different materials (e.g., a core region can be composed of a first material and a shell region can be composed of a second material) and/or have different functionalities (e.g., magnetic functionality, .controlled degradation functionality, buoyancy functionality, density-based functionality, etc.) In some embodiments there may be multiple regions either as multiple shell regions, or in other configurations such as amorphous or ordered spatial arrangements.

2.2 First Subset of Molecules—Target Capture

As shown in FIG. 1A, the composition 100 includes a first subset of molecules 120 (e.g., single cell analyte capture molecules) coupled to the body 110 and configured for target analyte capture, where a unit of the first subset 120 can include one or more of: a barcode segment (B) 122, a unique molecule identifier (M) 123, and a capture probe 124 (e.g., capture portion). The first subset of molecules 120 functions to provide desired chemistries (e.g., binding chemistries) for capture of targets from a sample being processed, in a manner that allows for subsequent processing and unique identification of the captured target material (e.g., using high throughput sequencing techniques). Molecules of the first subset of molecules 120 can be nucleic acid-based, with natural and/or modified nucleotides. Additionally or alternatively, molecules of the first subset can include oligonucleotide-conjugated antibodies (e.g., for protein-associated analyses).

As shown in FIG. 1A, the first subset of molecules 120 can include a barcode segment (B) 122 coupled to the body 110 (e.g., with a linker or anchor segment), which functions to provide a label that identifies the unique particle to which the molecule is coupled. The barcode segment (B) 122 is configured to be unique to each particle. Furthermore, the barcode segment (B) 122 is configured to have diversity such that each particle in a solution of particles can be uniquely identified (e.g., based on Poisson statistics). The barcode segment (B) 122 or other segments of molecules can be synthesized by way of chemical split-pool synthesis, enzymatic split-pool synthesis (e.g., by polymerase extension or ligation), or another suitable synthesis method.

An example method for producing functionalized particles can implement emulsion PCR (emPCR) to generate the functionalized particles. In more detail, the method 50 can include ligation of forward and reverse adaptor sequences to precursors of the molecule segment(s) described above, with optional restriction enzyme recognition sites adjacent the PCR primer sites to provide a targeted digestion/cleavage mechanism (other variations of cleavage mechanisms are described in more detail below) associated with a downstream step of functionalized particle generation. Then, the precursor molecules can be coupled to bead bodies as a distribution of forward primer and reverse primer precursor molecules coupled to the bead bodies, thereby producing dual primer-coupled beads. The method can then include mixing the dual primer-coupled beads with nucleic acid fragments, emulsion PCR reagents, and free primers with a phase (e.g., oil phase) that is immiscible with the bead solution. The emulsion is then thermocycled to produce an amplified product, followed by digestion/cleavage at the restriction enzyme recognition sites. Finally, specific anchor primers can be hybridized at the end of the forward and reverse strands. Then, following emulsion bead barcode generation, the method can implement one or more ligation-based methods to add UMI segments in bulk to the molecules of the functionalized particles.

In alternative variations, molecules of the functionalized particles can be synthesized by another suitable method (e.g., chemical split pool synthesis, enzymatic split pool synthesis, etc.).

In some cases, the barcode segment (B) 122 can have from 5-35 bases in order to provide a sufficient number of unique sequences for a desired number of particles in solution for a given process (i.e., such that each particle can be uniquely identified). Furthermore, the number of bases can be tuned based upon the number of intended particles per partition, where association of beads in the partition, each having different barcode sequences, produces another degree of uniqueness in terms of barcode sequence variation and length for each partition. However, in alternative variations, the barcode segment (B) 122 can have other suitable numbers of bases.

Figure 2:
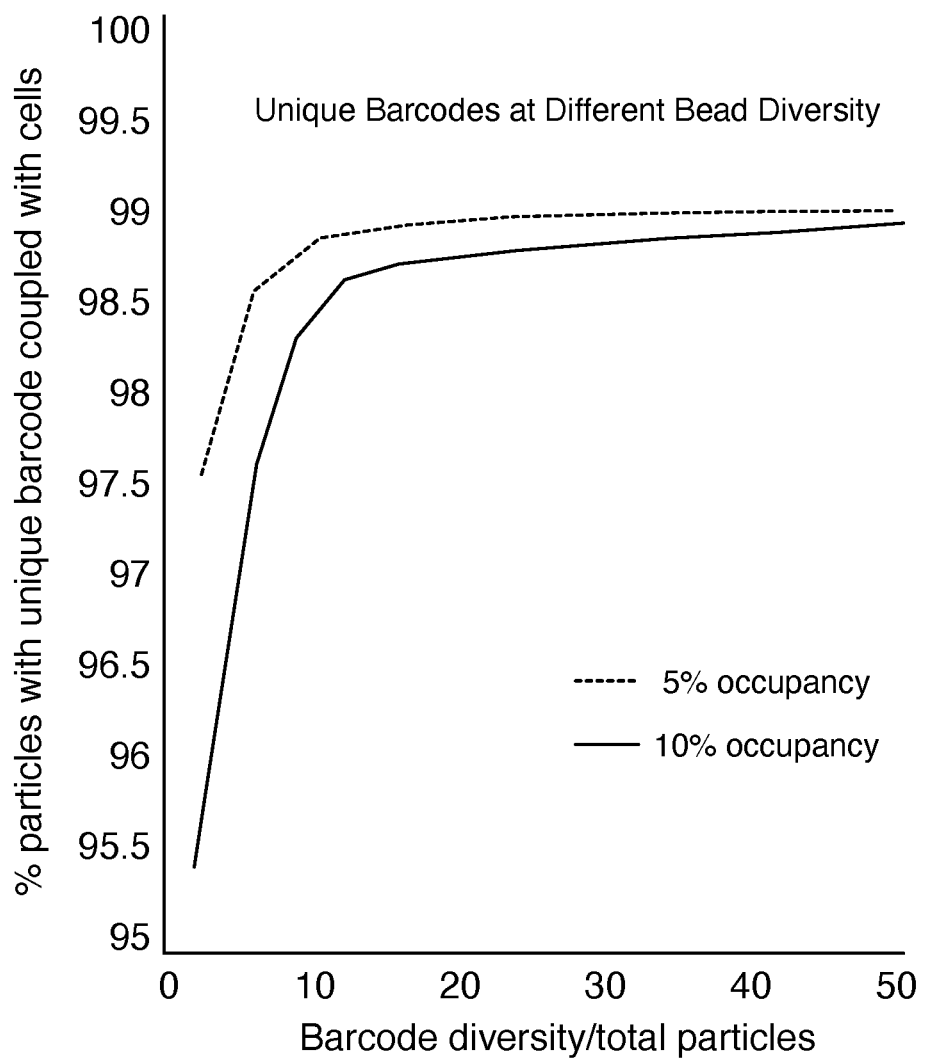
FIG. 2 depicts an example model output relating percent of particles with unique barcodes coupled with single cells as a function of barcode diversity, total number of particles, and percent occupancy by cells.

In more detail with respect to design of the barcode segments 122, in order to achieve a unique barcode library for each cell, every particle within a partition should have a unique barcode segment. As shown in FIG. 2, for a characteristic set of functionalized particles (by which a set of functionalized particles in use can be represented), the percentage of particles with unique barcodes coupled with target material from single cells can be a function of the barcode diversity (d) and number (n) of particles implemented, as well as the percent occupancy (o) of partitions by individual cells. As such, percentage=f(d, n, o). In examples taken from the modeled functions for 5% occupancy of partitions (blue line in FIG. 2) and 10% occupancy of partitions (orange line in FIG. 2): for a 10% occupancy condition, barcode diversity (d) should be 5× the total number of particles in all partitions to provide a 99% of particles with unique particles coupled with target material from single cells (e.g., if the percentage (p) is greater than 99%, the percent occupancy (o) of partitions is less than 10%, and the barcode diversity (d) is greater than five times the second number (n) of functionalized particles); for a 10% occupancy condition, barcode diversity (d) should be lox the total number of particles in all partitions to provide a 99.5% of particles with unique particles coupled with target material from single cells; and for a 10% occupancy condition, barcode diversity (d) should be 50× the total number of particles in all partitions to provide a 99.9% of particles with unique particles coupled with target material from single cells. The required barcode diversity can, however, be adjusted based upon barcode diversity (d), number (n) of particles implemented, and percent occupancy (o) of partitions by individual cells in another suitable manner.

As shown in FIG. 1A, the first subset of molecules 120 can also include a unique molecule identifier (M) 123, which functions to provide a label that identifies the unique molecule captured by the capture probe 124 during use of the composition. The unique molecule identifier (M) 123 is configured to have diversity such that the target molecules in its vicinity can be uniquely labeled (e.g., based on Poisson statistics).

The unique molecule identifier (M) 123 can be specific to various sequencing platforms (e.g., next generation sequencing platforms). Furthermore, each of the first subset of molecules 120 can have a single unique molecule identifier (M) 123 or multiple unique molecule identifier (M) 123 segments (e.g., to provide further diversity). The unique molecule identifier (M) 123 can be configured to not end in specific bases (e.g., GG) (or other sequences that are less suitable for specific sequencing platforms); however, the barcode segments can be configured in another suitable manner. Sequences of the unique molecule identifier (M) 123 across all molecules coupled to a particular body 110 can be configured through manufacturing to have a high degree of consistency (e.g., in relation to minimizing unintentional deletions, substitutions or additions) in order to produce low error rates during use.

Furthermore, in relation to the barcode segment (B) 122, the diversities of sequences of the unique molecule identifier (M) 123 and the barcode segment (P) 122 can be achieved by manufacture of a set random sequences, or alternatively, by a set of predetermined sequences.

In some cases, the unique molecule identifier (M) 123 can have from 5-20 bases in order to provide a sufficient number of unique sequences for a desired number of target molecules intended for capture (i.e., such that each target can be uniquely identified); however, in alternative variations, the unique molecule identifier (M) 123 can have other suitable numbers of bases. The unique molecule identifier (M) 123 can be directly coupled to the barcode segment (B) 122 (e.g., as shown in FIG. 1A) or can be alternatively configured in relation to position along a molecule of the first subset of molecules 120.

As shown in FIG. 1A, the first subset of molecules 120 can include a capture probe 124, which functions to capture target material (e.g., target nucleic acid capture from a lysed cell of the set of single cells) from an individual cell isolated with particles in a partition. The capture probe 124 can be directly coupled to the unique molecule identifier (M) 123 or can alternatively configured in relation to position along a molecule of the first subset of molecules 120. In variations, analytes captured by the capture probe can include: nucleic acids (e.g., DNA, mRNA, miRNA etc.) and/or oligonucleotides attached to other types of molecules (e.g., antibodies, proteins, peptides, chemicals, etc.).

Figure 3A:
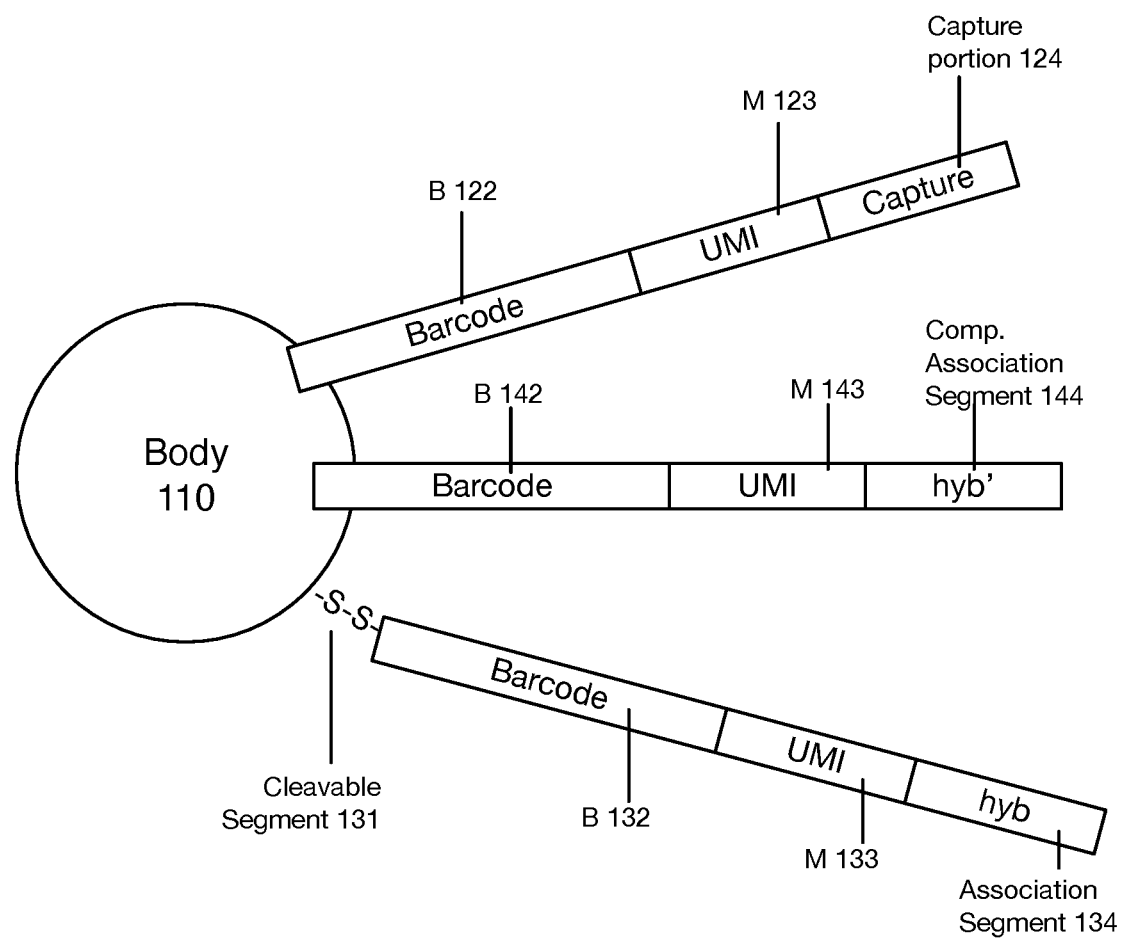
FIGS. 3A and 3B depict schematics of variations of particles for single cell barcoding and sequencing.
Figure 3B:
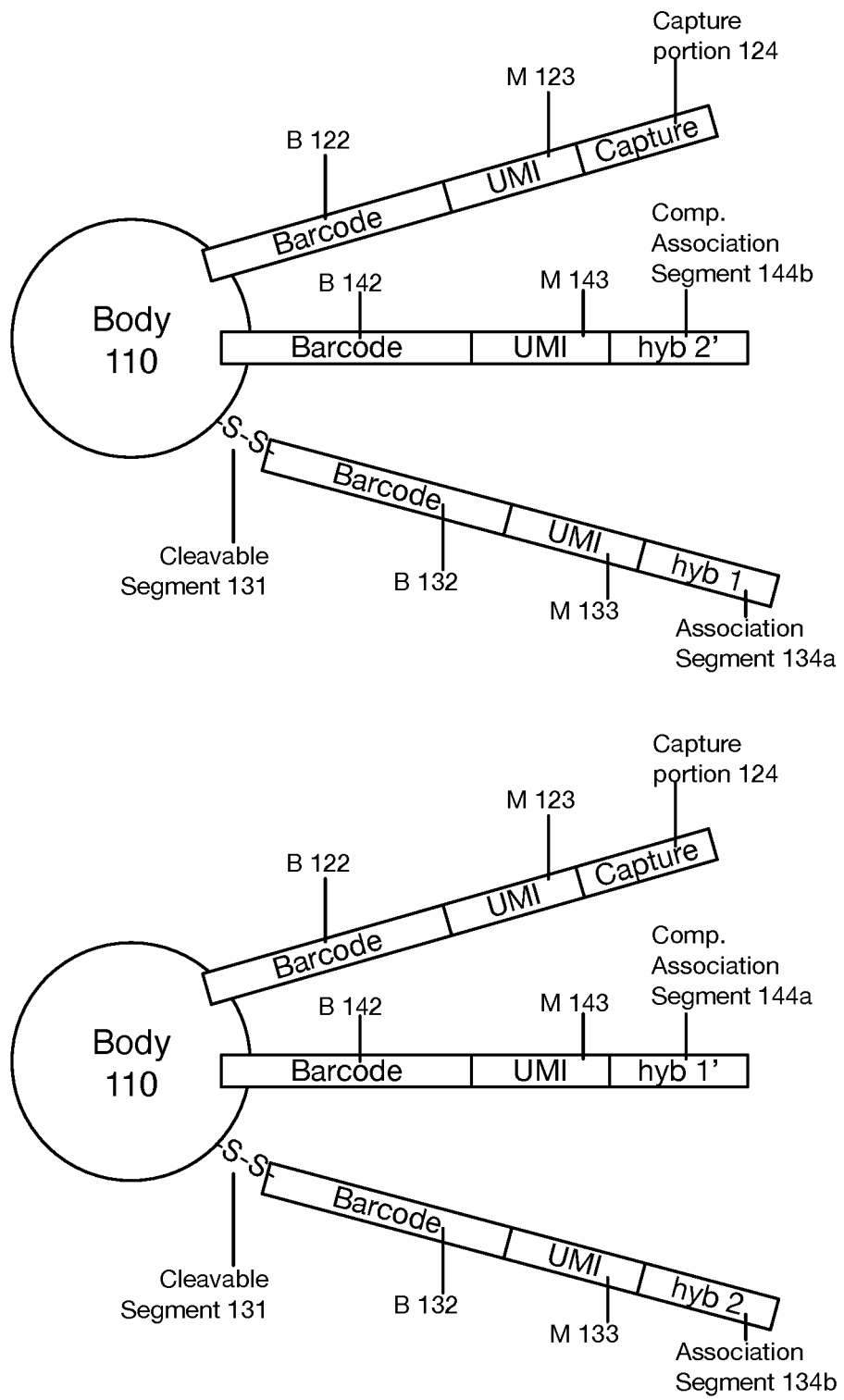

In one variation, as shown in FIGS. 3A-3B, the capture probe 124 can be configured for target mRNA binding (e.g., dT, dTVN for capturing polyA mRNAs, gene specific sequences). Capture of target mRNAs can then be followed by reverse transcription to append the capture probe portions of the first subset of molecules 120 with cDNA (e.g., as shown in FIG. 3A). Then, after amplification of the synthesized cDNA, high throughput sequencing can be used to read out the target molecules captured using the first subset of molecules 120. In alternative variations, inclusion of other capture probe types in the first subset of molecules 120 can configure the first subset of molecules 120 for capture of one or more of: DNA, other RNA (e.g., miRNA), proteins (e.g., antibodies, using TotalSeq™ molecules), small molecules, single analytes, multianalytes, etc.), and/or other target material. For nucleic acid targets, capture probes 124 of the first subset of molecules 120 can include complementary molecules to the nucleic acid targets. For protein targets or small molecule targets, capture probes 124 of the compositions described can include nucleic acids (e.g., oligonucleotide-conjugated antibodies), where targets of a sample (e.g., proteins, peptides, antibodies, small molecules, etc.) are tagged with an oligonucleotide having a sequence complementary to that of the capture probes 124.

Units of the composition can be configured with a sufficient number of capture probes 124 (e.g., total number per particle, total number bound to particles in solution) for efficient capture of target material (e.g., ~tens of thousands of mRNA molecules per cell, another number of targets per sample type). In variations, the average number of particles in a partition multiplied by the number of capture probes 124 per particle can be 10-100× (e.g., in terms of molarity, in terms of another concentration unit, etc.) the number of targets intended for capture.

In variations, units of the first subset of molecules 120 can omit or include additional segments as needed. For instance, one or more of the first subset of molecules 120 can include segments configured to simplify library preparation steps or sequencing processes of specific sequencing platforms. In more detail, molecules of the first subset of molecules 120 can include anchor/linker segments configured to couple the molecules to the body 110, adapter segments for polymerase chain reaction (e.g., associated with P5/P7 adapters for Illumina™ platforms), index sequences associated with adapters, and/or other sequences. Additionally or alternatively, additional segments can be added during sample processing (e.g., during reverse transcription, etc.). Units of the first subset of molecules 120 can additionally or alternatively include other sequences (e.g., for other processing platforms).

2.3 Second and Third Subsets of Molecules—Linking of Particles in a Partition In some cases, as shown in FIGS. 1A and 3A-3B, the set of molecules 115 can include a second subset of molecules 130 (e.g., releasable molecules) coupled to the body 110, where a unit of the second subset 130 includes a cleavable segment 131 configured to release the second subset from the body 110 in a controlled manner (e.g., in response to a trigger), the barcode segment (B) 132, the unique molecule identifier (M) 133, and an association segment 134.

In some cases, as shown in FIGS. 1A and 3A-3B, the set of molecules 115 can include a third subset of molecules 140 (e.g., hybridization molecules) coupled to the body 110, where a unit of the third subset 130 includes, the barcode segment (B) 142, the unique molecule identifier (M) 143, and a complementary association segment 144 configured to hybridize (e.g., preferentially hybridize, hybridizable) with the association segment 134 of a unit of the second subset of molecules 130 (e.g., of other association segments of other functionalized particles of the set of functionalized particles), when the second subset 130 is released from the body 110. The second and third subsets of molecules function to complement each other and provide a mechanism for linking all particles captured in a partition with a single cell.

Molecules of the second subset 130 and third subset 140 can be nucleic acid-based, with natural and/or modified nucleotides. Molecules of the second subset 130 and third subset 140 can be randomly interspersed with molecules of the first subset of molecules 120 about the body 110 or can alternatively be non-randomly distributed about the body 110 relative to molecules of the first subset of molecules 120 (e.g., in a desired ratio to promote linking reactions between units of the second and third subsets of molecules).

As shown in FIG. 1A, the second subset 130 and third subset of molecules 140 can include the barcode segment (B) 132, 142, which functions to provide a label that identifies the unique particle to which the molecule is coupled. As described above, the barcode segment (B) 132, 142 is configured to be unique to each particle and configured to have diversity such that each particle in a solution of particles can be uniquely identified (e.g., based on Poisson statistics). The barcode segments (B) 132, 142 can be identical (e.g., in sequence) to the barcode segment (B) 122 of the first subset of molecules 120 for target capture (e.g., to facilitate efficiency of synthesis of particle identification segments) or can alternatively be non-identical to the barcode segment (B) 122 of the first subset of molecules 120.

As shown in FIG. 1A, the second subset 130 and third subset of molecules 140 can include the unique molecule identifier (M) 133, 143, which functions to provide a label that identifies the unique molecule captured by the capture probe 124 during use of the composition. As described above, the unique molecule identifier (M) 133, 143 is configured to have diversity such that the target molecules in its vicinity can be uniquely labeled (e.g., based on Poisson statistics). The unique molecule identifier (M) 133, 143 can be specific to various sequencing platforms (e.g., next generation sequencing platforms), and the unique molecule identifier (M) 123 can be configured to not end in specific bases (e.g., GG) (or other sequences that are less suitable for specific sequencing platforms). Sequences of the unique molecule identifier (M) 133, 143 across all molecules coupled to a particular body 110 can be configured through manufacturing to have a high degree of consistency (e.g., in relation to minimizing unintentional deletions, substitutions or additions) in order to produce low error rates during use. The UMI (M) 133, 143 can be identical (e.g., in sequence) to the UMI (M) 123 of the first subset of molecules 120 or can alternatively be non-identical to the UMI (M) 123 of the first subset of molecules 120. Furthermore, in relation to the barcode segment (P) 122, the diversities of sequences of the unique molecule identifier (M) 123 and the barcode segment (P) 122 can be achieved by manufacture of a set random sequences, or alternatively, by a set of predetermined sequences.

As shown in FIGS. 1A-1D and 3A-3B, the second subset 130 includes a cleavable segment 131 configured to release the second subset from the body 110 in a controlled manner, and an association segment 134 configured to facilitate hybridization with complementary segments of other particles in a partition, thereby effectively linking the particles in a partition in a manner that can be identified post-sequencing. Units of the third subset of molecules 140 include a complementary association segment 144 configured to hybridize with the association segment 134 of a unit of the second subset of molecules 130, when the second subset 130 is released from the body 110. Furthermore, the complementary association segment 144 of a functionalized particle can be configured to be non-hybridizing with the association segment 134 of the functionalized particle, such that molecules of a respective functionalized particle do not self-hybridize.

The cleavable segment 131 can be configured to reversibly cleave by one or more of: an enzymatic triggering mechanism (e.g., restriction enzyme, restriction endonuclease, restrictase, etc.), a photocleaving triggering mechanism (e.g., with use of UV wavelength light, with use of other light), a pH shift triggering mechanism, another chemical cleaving mechanism, a heat triggering mechanism, and another suitable cleaving mechanism. As such, the trigger can include a compound selected from the group consisting of: an enzymatic trigger, a photocleaving trigger, a pH trigger, and a heat trigger. In an example, the cleavable segment 131 includes a disulfide bond, providing a controlled cleavage mechanism by dithiothreitol (DTT) at alkaline pH in order to release units of the second subset 130 for hybridization with complementary units of the third subset 140 of molecules.

As shown in FIGS. 1A-1D and 3A, the association segment 134 is configured to facilitate hybridization with complementary segments of other particles in a partition, upon cleavage of the cleavable segment 131, thereby effectively linking the particles in a partition in a manner that can be identified post-sequencing. Units of the third subset of molecules 140 include a complementary association segment 144 configured to hybridize with the association segment 134 of a unit of the second subset of molecules 130 (across different particles within a partition), when the second subset 130 is released from the body 110.

The association segment 134 can include an oligonucleotide sequence (e.g., 5-20 bases long, another suitable length), as depicted by [bead hyb] in FIG. 3A. The complementary association sequence 144 can have an oligonucleotide sequence that is complementary to the association sequence 134, as depicted by [bead hyb'] in FIG. 3A.

In the variation shown in FIG. 3B the association segment 134 and complementary association segment 144, as the direct complement of the association segment 134, can be configured to prevent self-hybridization, such that the molecules of a particle do not self-hybridize, or preferentially hybridize across particles within a partition. The complementary association segment of the functionalized particle is thus non-hybridizing (or non-preferentially hybridizing) with the association segment of the functionalized particle. As such, as shown in FIG. 3B, a first association segment 134a of a first particle 110a can include an oligonucleotide sequence as depicted by [bead hyb 1] in FIG. 3B, with a first complementary association sequence 144a coupled to second particle nob and having an oligonucleotide sequence that is complementary to the first association sequence 134a, as depicted by [bead hyb 1'] in FIG. 3B. Similarly, a second association sequence 134b of a second particle nob can include an oligonucleotide sequence as depicted by [bead hyb 2] in FIG. 3B, with a second complementary association sequence 144b coupled to first particle 110a and having an oligonucleotide sequence that is complementary to the first association sequence 134b, as depicted by [bead hyb 2'] in FIG. 3B. Such a configuration prevents self-hybridization of molecules originally bound to a particle, and promotes hybridization across different particles within a partition. While two association sequence/complementary association sequence pairs are depicted in FIG. 3B, another suitable number of association sequence/complementary association sequence pairs can be implemented in order to prevent self-hybridization and/or prevent situations in which particles within a partition do not have a complementary sequence for linkage. For instance, each particle can include a set of association sequences and non-complementary association sequences, in order to improve probabilities of being grouped in a partition in which the cleavable portion has a complementary structure to hybridize with.

Furthermore, in variations in which multiple complementary association sequences are used, corresponding cleavable segments can be configured to cleave by different mechanisms, thereby providing mechanisms for controlled release of segments for hybridization (e.g., in stages), in order to associate particles within a partition without encouraging self-hybridization.

While embodiments, variations, and examples of the composition 100 are described above, the composition 100 can be configured in another suitable manner to promote association of particles captured in a partition with single cell material, in an identifiable manner.

3. Methods

Figure 4A:
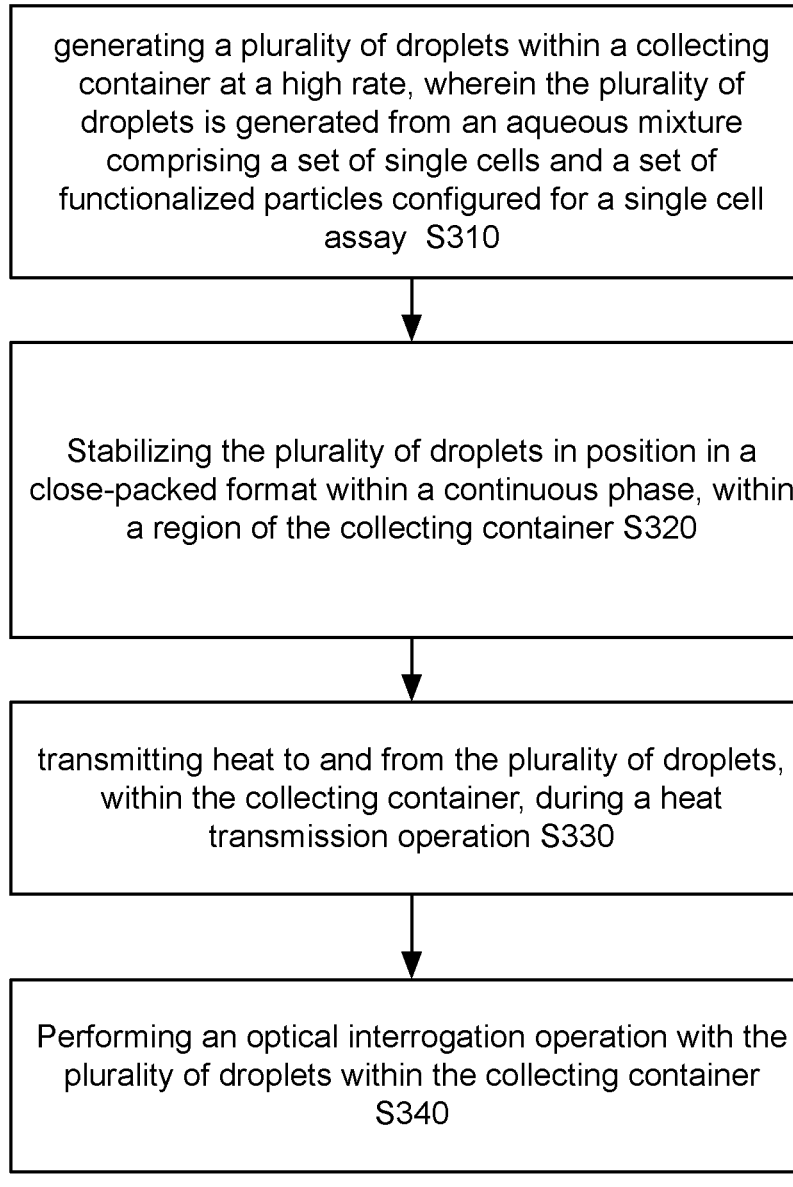
FIG. 4A depicts an embodiment of a method for single cell partitioning and processing.

As shown in FIG. 4A, an example of a method 300 for generation of droplets can include: generating a plurality of droplets within a collecting container at a high rate, wherein the plurality of droplets is generated from an aqueous mixture comprising a set of single cells and a set of functionalized particles configured for a single cell assay S310. In embodiments, upon generation, the plurality of droplets is stabilized in position in a close-packed format (e.g., three-dimensional close-packed format, hexagonal close-packed format, rectangular close-packed format, etc.) within a continuous phase, within a region of the collecting container S320.

Embodiments of the method 300 may function to generate a plurality of droplets at an extremely high and unprecedented rate in the context of single cell partitioning and other assays, where the droplets are stabilized in position (e.g., in a close-packed format, in equilibrium stationary positions) within a collecting container. Embodiments of the method 300 may further function to reliably generate droplets in a consistent and controlled manner (e.g., as monodisperse and uniform droplets having little-to-no polydispersity) for various applications including capture of target material at cellular, subcellular, and molecular scales; sample analysis benefitting from droplet generation; and/or other suitable applications. Embodiments of the method 300 may function to generate droplets using devices that are non-microfluidic, disposable or reusable, in a cost-effective manner.

Figure 1D:
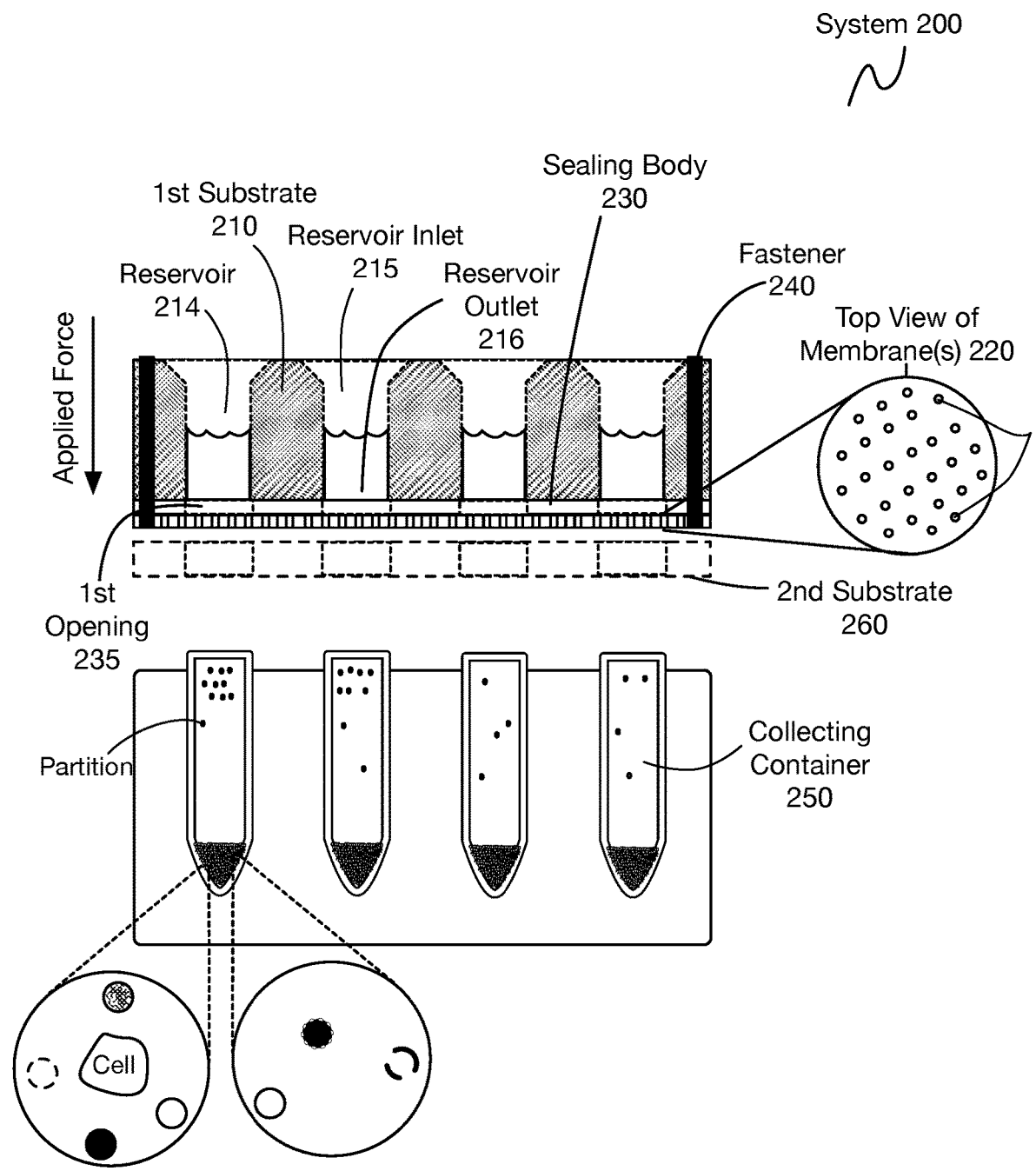
FIG. 1D depicts a schematic of an embodiment of a system for single cell partitioning and processing.

Embodiments, variations, and examples of the methods described can be implemented by or by way of embodiments, variations, and examples of components of system 200 shown in FIG. 1D, with a first substrate 210 defining a set of reservoirs 214 (for carrying sample/mixtures for droplet generation), each having a reservoir inlet 215 and a reservoir outlet 216; one or more membranes (or alternatively, droplet-generating substrates) 220 positioned adjacent to reservoir outlets of the set of reservoirs 214, each of the one or more membranes 220 including a distribution of holes 225; and optionally, a sealing body 230 positioned adjacent to the one or more membranes 120 and including a set of openings 235 aligned with the set of reservoirs 214; and optionally, one or more fasteners (including fastener 240) configured to retain the first substrate 210, the one or more membranes 220, and optional sealing body 230 in position relative to a set of collecting containers 250. In variations, the system 100 can additionally include a second substrate 260, wherein the one or more membranes 220 and optionally, the sealing body 230, are retained in position between the first substrate 210 and the second substrate 260 by the one or more fasteners.

In variations, the distribution of holes 120 can be generated in bulk material with specified hole diameter(s), hole depth(s) (e.g., in relation to membrane thickness), aspect ratio(s), hole density, and hole orientation, where, in combination with fluid parameters, the structure of the membrane can achieve desired flow rate characteristics, with reduced or eliminated polydispersity and merging, suitable stresses (e.g., shear stresses) that do not compromise the single cells but allow for partitioning of the single cells, and steady formation of droplets (e.g., without jetting of fluid from holes of the membrane).

In variations, the hole diameter can range from 15 micrometers to 200 micrometers, and in examples, the holes can have an average hole diameter can be 15 micrometers, 20 micrometers, 30 micrometers, 40 micrometers, 50 micrometers, 60 micrometers, 70 micrometers, 80 micrometers, 90 micrometers, 100 micrometers, 150 micrometers, 200 micrometers, any intermediate value, or greater than 200 micrometers (e.g., with use of membrane having a suitable thickness).

In variations, the hole depth can range from 1 micrometer to 200 micrometers (e.g., in relation to thickness of the membrane layer) or greater, and in examples the hole depth (e.g., as governed by membrane thickness) can be 1 micrometers, 5 micrometers, 10 micrometers, 20 micrometers, 30 micrometers, 40 micrometers, 50 micrometers, 60 micrometers, 70 micrometers, 80 micrometers, 90 micrometers, 100 micrometers, 125 micrometers, 150 micrometers, 175 micrometers, 200 micrometers, or any intermediate value.

In variations, the hole aspect ratio can range from 5:1 to 200:1, and in examples, the hole aspect ratio can be 5:1, 10:1, 20:1, 30:1, 40:1, 50:1, 60:1, 70:1, 80:1, 90:1, 100:1, 125:1, 150:1, 175:1, 200:1, or any intermediate value.

In variations, the hole-to-hole spacing can range from 20 micrometers to 200 micrometers or greater, and in examples, the hole-to-hole spacing is 20 micrometers, 30 micrometers, 40 micrometers, 50 micrometers, 60 micrometers, 70 micrometers, 80 micrometers, 90 micrometers, 100 micrometers, 125 micrometers, 150 micrometers, 175 micrometers, 200 micrometers, or greater. In a specific example, the hole-to-hole spacing is greater than 10 micrometers.

In examples, the hole orientation can be substantially vertical (e.g., during use in relation to a predominant gravitational force), otherwise aligned with a direction of applied force through the distribution of holes, or at another suitable angle relative to a reference plane of the membrane or other droplet generating substrate 120.

Additionally or alternatively, embodiments, variations, and examples of the methods described can be implemented by or by way of embodiments, variations, and examples of components described in U.S. application Ser. No. 17/687,080 filed 4 Mar. 2022 and U.S. Pat. No. 11,242,558 granted 8 Feb. 2022, each of which is herein incorporated in its entirety by this reference.

3.1 Methods—Droplet Generation

In relation to generation of droplets at a high rate in Step S310, variations of the method 300 can produce droplets at a rate of at least 10,000 droplets/minute, of at least 20,000 droplets/minute, of at least 30,000 droplets/minute, of at least 40,000 droplets/minute, of at least 50,000 droplets/minute, of at least 100,000 droplets/minute, of at least 200,000 droplets/minute, of at least 300,000 droplets/minute, of at least 400, droplets/minute, of at least 500,000 droplets/minute, of at least 600,000 droplets/minute, of at least 700,000 droplets/minute, of at least 800,000 droplets/minute, of at least 900,000 droplets/minute, of at least 1 million droplets/minute, of at least 2 million droplets/minute, of at least 3 million droplets/minutes, or greater, using embodiments, variations, and examples of system elements described above. Droplets can be generated at the high rate, using embodiments, variations, and examples of the membrane(s) or other substrates (e.g., microchannel array plates) described in Applications and Patents incorporated by reference above, in relation to hole density, hole-to-hole spacing, hole diameter, membrane thickness, hole aspect ratio, membrane material, and/or other characteristics.

In relation to droplet generation in Step S310, an extremely high number of droplets can be generated within a collecting container, wherein, in variations, greater than 2 million droplets, greater than 3 million droplets, greater than 4 million droplets, greater than 5 million droplets, greater than 6 million droplets, greater than 7 million droplets, greater than 8 million droplets, greater than 9 million droplets, greater than 10 million droplets, greater than greater than 15 million droplets, greater than 20 million droplets, greater than 25 million droplets, greater than 30 million droplets, greater than 40 million droplets, greater than 50 million droplets, greater than 100 million droplets, greater than 200 million droplets, greater than 300 million droplets, or greater can be generated within the collecting container.

In variations, the collecting container can have a volumetric capacity less than 100 microliters or from 100 through 1 milliliter and greater. An example of a collecting container can include a PCR strip tube or conical tube; however, other variations and examples of collecting containers are described in Applications and Patents incorporated by reference above. Droplets generated in Step S310 may have a characteristic dimension (e.g., from 1-60 micrometers, from 10-30 micrometers, intermediate values within ranges described, etc.) that is relevant for single cell capture, target detection, individual target partitioning, or other applications.

Generating the plurality of droplets in Step S310 can include driving a sample fluid through a membrane or other substrate (e.g., microchannel array plate) comprising a distribution of holes, the membrane or other substrate aligned with or coupled to a reservoir outlet of a reservoir for the sample fluid. The membrane/substrate can be coupled to a reservoir outlet of a reservoir for the sample fluid and the collecting container can be aligned with the substrate, downstream of the substrate, in order to receive the generated droplets. As such, methods described can include distributing a set of single cells and a set of functionalized particles across a plurality of droplets of an emulsion (e.g., using systems and materials as described above), upon driving a mixture comprising the set of single cells and the set of functionalized particles through a substrate having a distribution of holes. In relation to generation of the emulsion, the mixture can be driven through the holes of the substrate into one or more fluid layers, such that the droplets are stabilized within an emulsion. Cytometry can be used to determine a suitable number of single cells to include in the mixture, such that each droplet generated likely contains one or zero single cells, and a subset of the set of functionalized particles, after the single cells are partitioned across the plurality of droplets.

Driving the sample fluid can include applying a centrifugal force (e.g., by centrifugation) to drive the sample fluid through the holes of the membrane. In variations, the centrifugal force can be applied at 1,000 g, 2,000 g, 3,000 g, 4,000 g, 5,000 g, 6,000 g, 7,000 g, 8,000 g, 9,000 g, 10,000 g, 11,000 g, 12,0000 g, 13,000 g, 14,000 g, 15,000 g, 16,000 g, 17,000 g, 18,000 g, 19,000 g, 20,000 g, 30,000 g, any intermediate value, or greater than 30,000 g. Duration of spinning can be 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 30 minutes, 40 minutes, 50 minutes, any intermediate value, or greater than 50 minutes, where spin duration is a function of the amount of sample fluid being dropletized.

However, in alternative variations, the applied force can be associated with an applied pressure, magnetically applied, or otherwise physically applied to drive sample fluid(s) through the membrane(s) or other substrates.

In relation to components of the sample fluid and/or fluid layers within the collecting container(s) for generation of an emulsion, the sample fluid and fluid layers within the collecting container can have one or more of a certain density, viscosity, surface tension, aqueous nature, hydrophobicity, immiscibility characteristics, or other characteristics. Fluids implemented can have densities from 1 through 3000 kg/m3 and intermediate values, viscosities from 0.001 through 0.1 Ns/m2, and surface tensions of 0.01 through 1 N/m, depending upon application. Sample fluids and/or fluid layers can further include materials described in U.S. Pat. No. 11,162,136 granted on 2 Nov. 2021, incorporated by reference above, where, in one such embodiment, a collecting container contains an oil layer covering an aqueous layer, and the sample fluid is driven through the substrate into the collecting container to generate an emulsion of the plurality of droplets separated from each other by a continuous phase. Further, droplets and/or resulting emulsions generated with said droplets can have a high degree and greater than a threshold level of clarity, with or without refractive index matching. In variations, the threshold level of clarity of the emulsion is associated with a transmissivity greater than 50% transmissivity, greater than 60% transmissivity, greater than 70% transmissivity, greater than 80% transmissivity, greater than 90% transmissivity, greater than 95% transmissivity, greater than 99% transmissivity, etc., upon measuring clarity of the emulsion using a transmission detector.

Materials of the emulsions described can further prevent leakage of single-cell contents (e.g., mRNAs, nucleic acids, nuclear components, proteins, other analytes, etc.) from one partition to another, thereby enabling isolation of single cell material throughout sample processing and downstream analyses.

In relation to single cell processing, and in addition to the set of single cells and the set of functionalized particles (i.e., embodiments, variations, and examples of functionalized particle compositions described in Section 2 above), the sample fluid (e.g., aqueous mixture of sample and other components) can additionally or alternatively include one or more of: fixing solution components (e.g., pre-fixing solution, post-fixing solution), buffer components (e.g., permeabilization buffers), lysis reagents, inhibitor reagents, cocktails (e.g., primary antibody cocktails, secondary antibody cocktails), stains (e.g., fluorescent stains, histological stains), and/or any other suitable fluids for cell capture or analysis.

Additionally or alternatively, in some variations, the sample fluid can include magnetic components that can be used to promote purification of partitioned cells/material derived from single-partitioned cells (e.g., during downstream processing), or to manipulate droplets containing single cell material by magnetic attraction or repulsion. Additionally or alternatively, magnetic components can be used to manipulate droplets not containing single cell material by magnetic attraction or repulsion, such that partitions without single cell material can be drawn away from partitions containing single cell material, controllably ruptured, or otherwise manipulated.

For instance, for purification, the sample fluid can contain solutions of magnetic particles coupled with affinity molecules configured to bind to components not of interest (e.g., undesired cells, fragments, waste products), in order to facilitate magnetic separation of such components in later processing steps, or controlled rupture of partitions not associated with single-cell material. Alternatively, for purification, the sample fluid can contain solutions of magnetic particles coupled with affinity molecules configured to bind to components of interest (e.g., target cells, other target analytes), in order to facilitate magnetic separation of such components in later processing steps. Additionally or alternatively, the sample fluid can contain solutions of magnetic particles configured to bind to components of interest (e.g., target cells, other target analytes), and application of a magnetic field to the collecting container (or to derivatives of the sample in later steps) can be used to attract or repel components of interest and/or partitions containing components of interest to desired surfaces of the collecting container or other container for analysis (e.g., by optical interrogation, for retrieval, etc.).

In embodiments, upon generation, the plurality of droplets can be stabilized in position in a close-packed format (e.g., three-dimensional close-packed format, hexagonal close-packed format, rectangular close-packed format, etc.) within a continuous phase, within a region of the collecting container S320. In relation to the membranes/substrates described, generating the plurality of droplets can include transmitting droplets (e.g., two dimensional arrays of droplets from the holes of the membrane(s)) toward a closed end of the collecting container, thereby stabilizing the plurality of droplets in a three dimensional close-packed format toward the closed end of the collecting container. Alternatively, the plurality of droplets can be stabilized (e.g., within a continuous phase, within a matrix positioned within the collecting container, within a mesh within the collecting container, etc.) toward the closed end or a different region of the collecting container, in a non-close-packed format. For instance, non-close packed droplets or droplets that can move relative to each other within the closed collecting container can still be processed by optical interrogation as described in more detail below (e.g., by fixing a position of the closed collecting container relative to a scanning path of an optical interrogation instrument). Additionally or alternatively, in relation to close-packed or non-close-packed formats, droplets of an emulsion can be stabilized in position by curing (e.g., with light, with heat, with a pH shift, with other cross-linking, by way of an electric field, by way of a magnetic field, etc.) the dispersed phase, continuous phase, or both of the emulsion. Still alternatively, droplets may not be stabilized in position or in a close-packed format (e.g., droplets can move relative to each other within a container, such as for water-in-oil or oil-in-water emulsions, etc.).

In some variations, as shown in FIG. 4A, the method 300 can further include: transmitting heat to and from the plurality of droplets, within the collecting container, during a heat transmission operation S330. Heat transmission can be associated with cold storage (e.g., refrigeration, freezing, etc.), lysis (e.g., for lysing the set of single cells within the plurality of droplets with the lysis reagent, and wherein individual droplets of the plurality of droplets remain unmerged with adjacent droplets during lysing), incubation, culture, thermocycling (e.g., during an amplification process), enzyme activation, or another heat transmission operation. In variations, the temperature may vary between 0° C. to 95° C. during the heat transmission operation, and in specific examples, the temperature can transition between temperatures within the ranges described, with stability of droplets maintained. In particular, given the droplet generation techniques and materials described, individual droplets of the plurality of droplets remain unmerged with adjacent droplets in the close-packed format during the heat transmission operation.

In some variations, as shown in FIG. 4A, the method 300 can further include: performing an optical interrogation operation with the plurality of droplets within the collecting container S340, where the optical interrogation operation can include readout of signals (e.g., light signals, fluorescent signals, colorimetric signals, etc.) from droplets of the plurality of droplets. In particular, readout can be performed for cross sections of the plurality of droplets within the collecting container, using techniques described in applications incorporated by reference.

In variations, readout of fluorescent signals (e.g., from labeled single-cell material from droplets of the dispersed phase, from other labeled analytes from droplets of the dispersed phase, from products of analytes from droplets of the dispersed phase, etc.) can be performed by one or more of a 3D scanning technique (e.g., light sheet imaging, confocal microscopy, etc.) and a planar imaging technique (e.g., to take images of a cross-section of the closed container). Additionally or alternatively, in some applications, readout of colorimetric changes associated with droplets of the dispersed phase can be performed by 3D imaging techniques (e.g., 3D brightfield construction using light field imaging, etc.). Readout can be performed for each of a set of cross sections of the plurality of droplets/collecting container, across multiple color channels (e.g., 2 color channels, three color channels, four color channels, five color channels, six color channels, seven color channels, etc.).

Readout associated with single-cell analyses can be performed for 10 cross-sections of the plurality of droplets, 20 cross-sections of the plurality of droplets, 30 cross-sections of the plurality of droplets, 40 cross-sections of the plurality of droplets, 50 cross-sections of the plurality of droplets, 60 cross-sections of the plurality of droplets, 70 cross-sections of the plurality of droplets, 80 cross-sections of the plurality of droplets, 90 cross-sections of the plurality of droplets, 100 cross-sections of the plurality of droplets, 200 cross-sections of the plurality of droplets, 300 cross-sections of the plurality of droplets, 400 cross-sections of the plurality of droplets, 500 cross-sections of the plurality of droplets, boo cross-sections of the plurality of droplets, 700 cross-sections of the plurality of droplets, any intermediate value, or greater, within the closed collecting container, for each of the set of color channels.

In specific examples, readout associated with digital analyses (e.g., counting, quantification, etc.) for each channel can be performed within a duration of 5 minutes, 4 minutes, 3 minutes, 2 minutes, 1 minute, 30 seconds, 20 seconds, 10 seconds, 5 seconds or less, depending upon one or more of signal-to-noise ratio, optical sensor sensitivity, excitation power (e.g., of a light source used to illuminate droplets and induce fluorescence), or other characteristics.

In other variations, readout of non-fluorescent signals from droplets of the dispersed phase can be performed. For instance, products resulting from reactions within individual droplets of the dispersed phase can produce changes in one or more of refractive indices, light absorption, light scattering, light reflection, light transmission, or other light interaction characteristics that are different from empty or unreacted droplets, for detection by various techniques (e.g., spectrophotometric techniques, turbidimetric techniques, etc.).

As such, methods described enable digital analyses of single cells across a wide dynamic range that is 10-100 times greater than that of existing technologies, depending upon application of use. In examples related to single cell assays, the methods disclosed herein can have a dynamic range from 1 through 100 million, due to the extremely high number of uniform partitions generated from which signals can be read, and due to the ability to partition with low occupancy (e.g., less than 20% occupancy, less than 15% occupancy, less than 10% occupancy, less than 9% occupancy, less than 8% occupancy, less than 7% occupancy, less than 6% occupancy, less than 5% occupancy, etc.) of partitions. In variations, such low occupancy can enable characterization of targets such as single cells of interest without requiring Poisson statistics-associated correction factors for partitioning error or other error.

In examples, generation of large numbers of droplets (as described) within a closed container can be performed within durations and at rates described (e.g., on the order of 1 million droplets/minute), and readout of each channel for a digital analysis can be performed at a high rate (e.g., less than 1 minute per channel, across multiple color channels), thereby enabling readout for a digital analysis of millions of partitions on the order of minutes or hours (with time durations described as above).

As such, methods for droplet generation through readout of numbers of droplets described, for each of a set of channels for a digital analysis, can be performed within a duration of 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, or any intermediate value. In examples, once droplet generation and amplification/tagging have been performed, readout of signals from each channel can be performed within 5 minutes, 4 minutes, 3 minutes, 2 minutes, 1 minute, 30 seconds, 20 seconds, 10 seconds, or less, depending upon one or more of signal-to-noise ratio, optical sensor sensitivity, excitation power (e.g., of a light source used to illuminate droplets and induce fluorescence), or other characteristics.

As such, methods for droplet generation through readout of numbers of droplets can include: performing a digital analysis of single-cell material from a sample within a duration (e.g., a duration described), wherein performing the digital analysis includes: generating a plurality of droplets (e.g., within a closed collecting container, the plurality of droplets comprising a number of droplets described generated from a combination of the sample and materials for an single-cell-associated assay, individually isolating the plurality of droplets (e.g., within a continuous phase of an emulsion), receiving heat (e.g., through the closed collecting container), thereby executing one or more processes described, and transmitting signals, (e.g., from a set of cross-sections of the emulsion comprising the plurality of droplets within the closed collecting container), for readout using a set of channels of a detection system (e.g., a detection system interacting with the closed collecting container).

Additional related method implementations are further described below.

3.1.1 Method—Implementation

As shown in FIG. 4B, a method 400 for uniquely associating content of a partition can include: providing a set of particles distributed across a set of partitions, wherein a subset of partitions of the set of partitions contain target material from isolated single cells, and wherein each of the set of particles includes a first subset of molecules for capture of the target material, and a second subset of molecules configured to react with a third subset of molecules upon release from the set of particles, to enable identification of associations between a subset of particles within a partition containing target material from the single cell S410; promoting selective capture of the target material by the first subset of molecules coupled to the subset of particles within the partition S420; triggering release of the second subset of molecules for interactions with the third subset of molecules S430; generating a set of amplifiable templates with linked barcode segments associated with the subset of particles within the partition, as a bead-linked library for sequencing S440; sequencing the set of amplifiable templates after combining material from the set of partitions S450; generating a network of linked barcodes from the set of amplifiable templates upon performing a set of operations S460; from the network of linked barcodes, determining a set of particle characteristics for each partition, wherein the set of particle characteristics includes a first factor describing the particles within a particular partition, and a second factor describing how many particles were within the particular partition S470; and from the set of particle characteristics, generating a single cell expression library from sequenced analytes associated with the set of particle characteristics for the particular partition S480.

Embodiments of the method 400 function to provide a novel mechanism for single cell analysis, that provides high capture efficiency without complex or expensive experimental apparatus. In variations, the method 400 can be implemented in a low-occupancy regime, in which only a small subset of a set of partitions contains single cells and/or target material from single cells, and the partitions are "superloaded" (as described above) with functionalized particles configured for capture of target material from the single cells. The functionalized particles thus have functionality for interacting with each other in a manner that allows for identification of the particular functionalized particles within a partition post-sequencing.

Embodiments of the method 400 also function to provide mechanisms for efficient capture and labeling of target material (e.g., DNA, RNA, miRNA, proteins, small molecules, single analytes, multianalytes, etc.) in order to characterize partitioned cells at single-cell resolution.

The method 400 can be enabled by embodiments, variations, and examples of the compositions described above, and/or other suitable systems and compositions.

3.1.1.1 Method—Partitioning of Functionalized Particles with Single Cells

Step S410 recites: providing a set of particles distributed across a set of partitions, wherein a subset of partitions of the set of partitions contain target material from isolated single cells, and wherein each of the set of particles includes a first subset of molecules for capture of the target material, and a second subset of molecules configured to react with a third subset of molecules upon release from the set of particles, to enable identification of associations between a subset of particles within a partition containing target material from the single cell. As described above, partitioning can be performed using droplets (e.g., of an emulsion), wells (e.g., microfluidic wells, nanofluidic wells), and/or other forms of physical partitioning of cells, sub-cellular structures (e.g., organelles), oligonucleotides, other individual targets, and/or other analytes. As described, each of a subset of the plurality of partitions/droplets can host one single cell of the set of single cells, and a subset of the set of functionalized particles (e.g., in an over-loading regime), upon distribution of cells and particles across the set of partitions.

The set of particles can include variations and examples of compositions described in Section 2 above.

3.1.1.2 Method—Target Capture of Material from Single Cells

Step S420 recites: promoting selective capture of the target material by the first subset of molecules coupled to the subset of particles within the partition, which functions to implement capture probes of a subset of molecules coupled to core bodies of the functionalized particles, as described above, to capture target material from each partitioned individual cell. Promoting selective capture can include processing the sample with the set of functionalized particles in a suitable environment (e.g., with respect to solution, temperature, pH, concentration of components, flow, washing, reagents, etc.). Additionally or alternatively, promoting selective capture can include other suitable processing steps (e.g., lysis of sample components, washing of undesired sample components, etc.).

In one variation, Block S420 can include capturing target mRNAs of the sample (e.g., using capture probes with dT, dTVN for capturing polyA mRNAs, or gene specific sequence), followed by reverse transcription to append the capture probes with cDNA. In alternative variations, block S420 can include promoting selective capture of one or more of: DNA, other RNA (e.g., miRNA), proteins (e.g., antibodies, using TotalSeq™ molecules), small molecules, single analytes, multianalytes, etc.), and/or other target material using suitable capture probes. As such, for nucleic acid targets, capture probes of a first subset of molecules coupled to the functionalized particles can include complementary molecules to the nucleic acid targets. For protein targets or small molecule targets, capture probes of a first subset of molecules coupled to the functionalized particles can include nucleic acid sequences, where targets of a sample (e.g., proteins, peptides, antibodies, small molecules, etc.) are tagged with an oligonucleotide having a sequence complementary to that of the capture probes 124.

3.1.1.3 Method—Linking Particles Within Each Partition

Figure 5A:
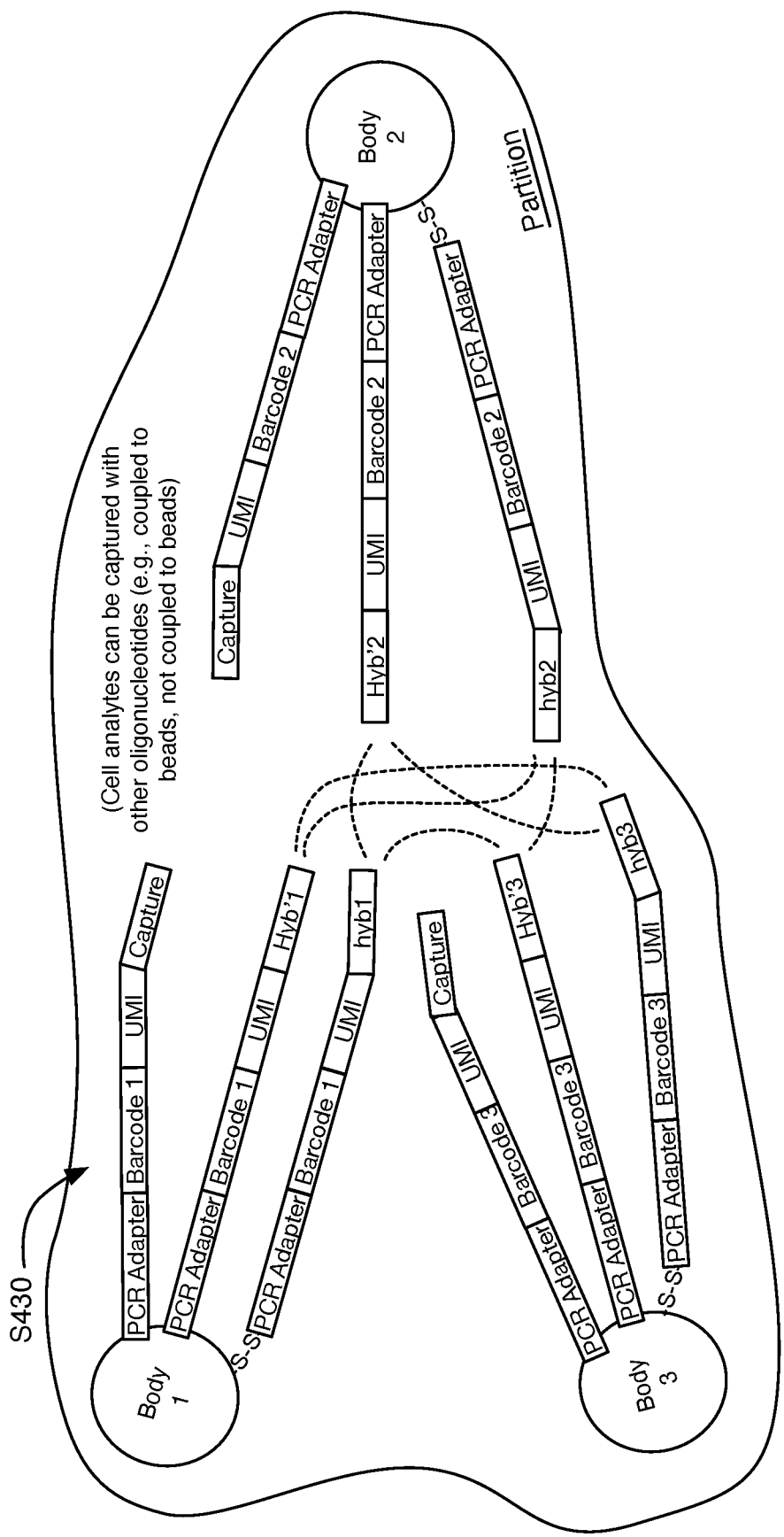
FIGS. 5A-5D depict variations of steps of a method for single cell barcoding and sequencing.

Step S430 recites: triggering release of the second subset of molecules for interactions with the third subset of molecules, which functions to release a portion of molecules coupled to each particle within a partition, for hybridization with complementary molecules on other particles within the partition, thereby enabling identification of the particles within the partition post-sequencing. Step S430 can include cleaving the second subset of molecules by way of: an enzymatic mechanism (e.g., restriction enzyme, restriction endonuclease, restrictase, etc.), a photocleaving mechanism (e.g., with use of UV wavelength light, with use of other light), a pH shift, another chemical cleaving mechanism, heat, or another suitable cleaving mechanism. In the example shown in FIGS. 1A, 3A, and 5A, each of the second subset of molecules can include a disulfide bond, and triggering release includes using dithiothreitol (DTT) at alkaline pH in order to release units of the second subset of molecules for hybridization with complementary units of the third subset of molecules. However, triggering release can be performed in another suitable manner.

3.1.1.4 Method—Amplification and Sequencing

Figure 5B:
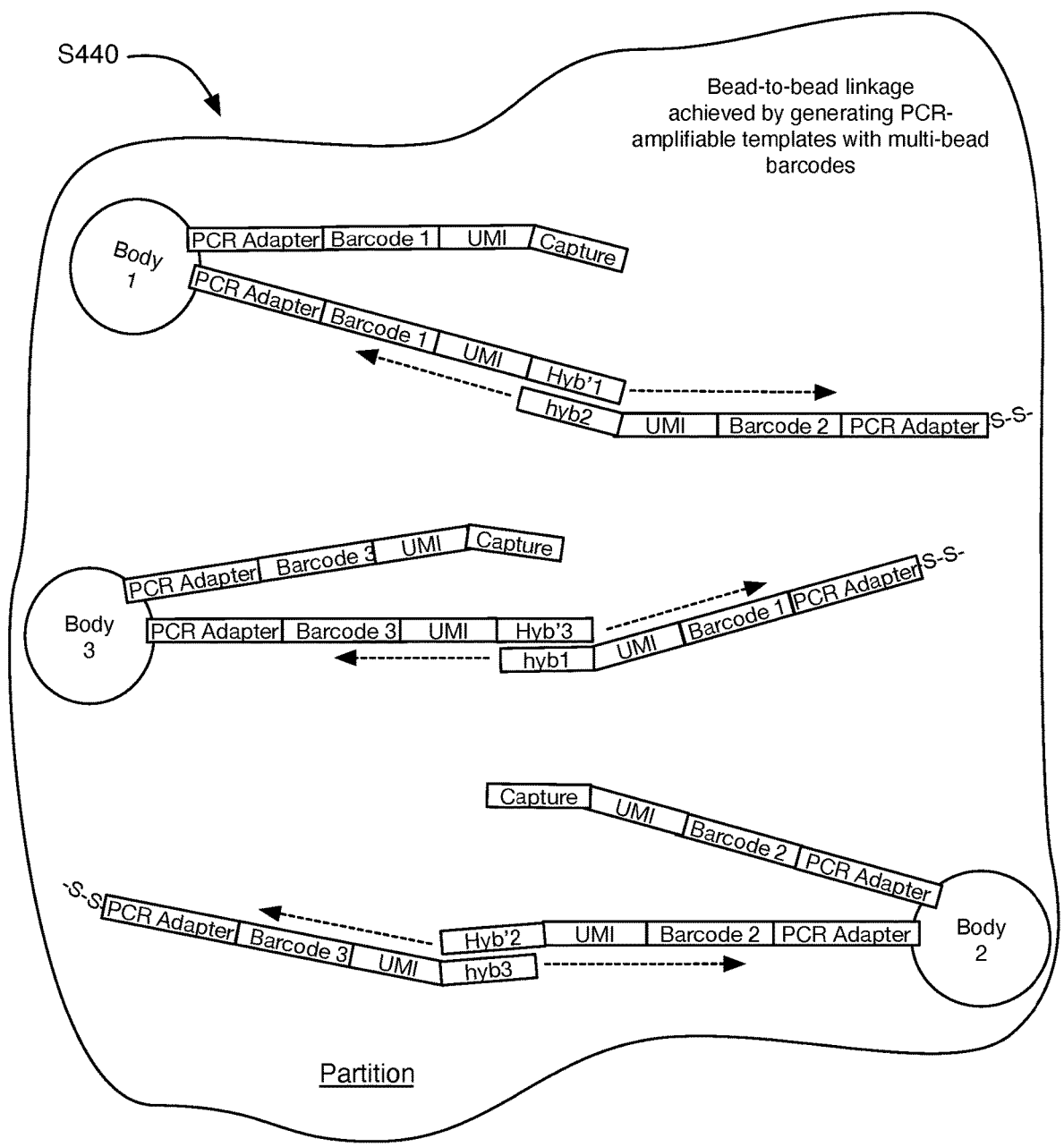

Step S440 recites: generating a set of amplifiable templates with linked barcode segments associated with the subset of particles within the partition, as a bead-linked library for sequencing, and Step S450 recites: sequencing the set of amplifiable templates after combining material from the set of partitions. Steps S440 and S450 function to hybridize complementary association segments (described above) for different particles within a partition, where the hybridized molecules generate amplifiable templates having multiple barcode sequences (i.e., one barcode sequence from each participating particle). In the example shown in FIG. 5B, released molecules of the second subset of molecules can hybridize with complementary molecules of the third subset of molecules on other particles within a partition, and amplifiable templates having two barcode sequences (e.g., a combination of B1 and B2, a combination of B2 and B3, a combination of B1 and B3) are generated. In variations of the specific example, other numbers of particles within a partition can be implemented.

Figure 5C:
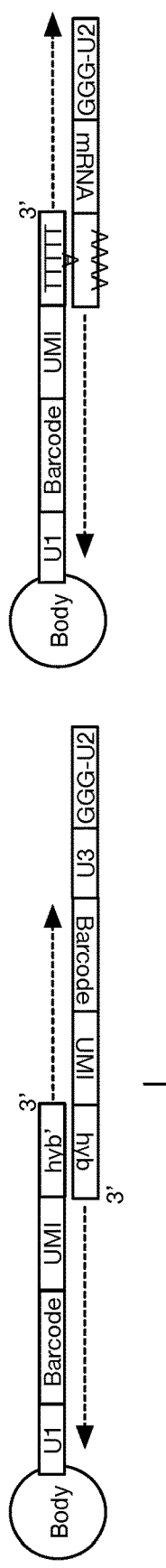
Figure 5C:
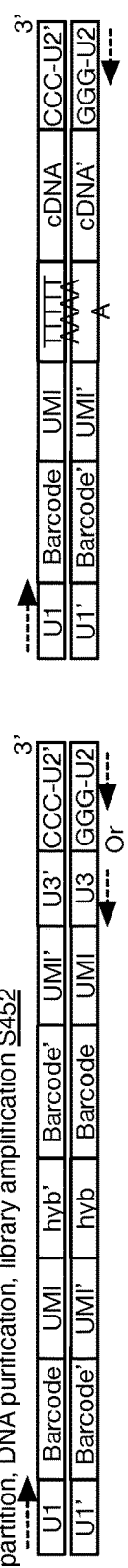

In Step S450, sequencing the set of amplifiable templates can include de-partitioning or otherwise combining partitions (e.g., breaking emulsions to combine partitions, extracting material from microwells or other arrays to combine partitions, combining droplets, etc), and implementing high throughput sequencing for readout of the amplifiable templates (e.g., post-amplification by PCR). Additionally or alternatively, other sequencing approaches can be used to readout the amplified templates. In the example shown in FIG. 5C, Step S450 can include performing a reverse transcription operation with template switching within each partition S451, followed by de-partitioning, nucleic acid purification, and library amplification S452, followed by amplified product purification and size selection (e.g., given that the bead-linked library is smaller than the target analyte capture library) S453, followed by subsequent steps to add sequencing adapters S454 (as discussed above) prior to sequencing.

As such, Step S450 can also include sequencing of target molecules captured by capture probes of the set of functionalized particles (e.g., post reverse transcription and amplification of synthesized cDNA, for mRNA applications described above). In one variation, high throughput sequencing can be used for readout of the target molecules captured. Additionally or alternatively, other sequencing approaches can be used for readout of the target molecules captured.

Figure 5D:
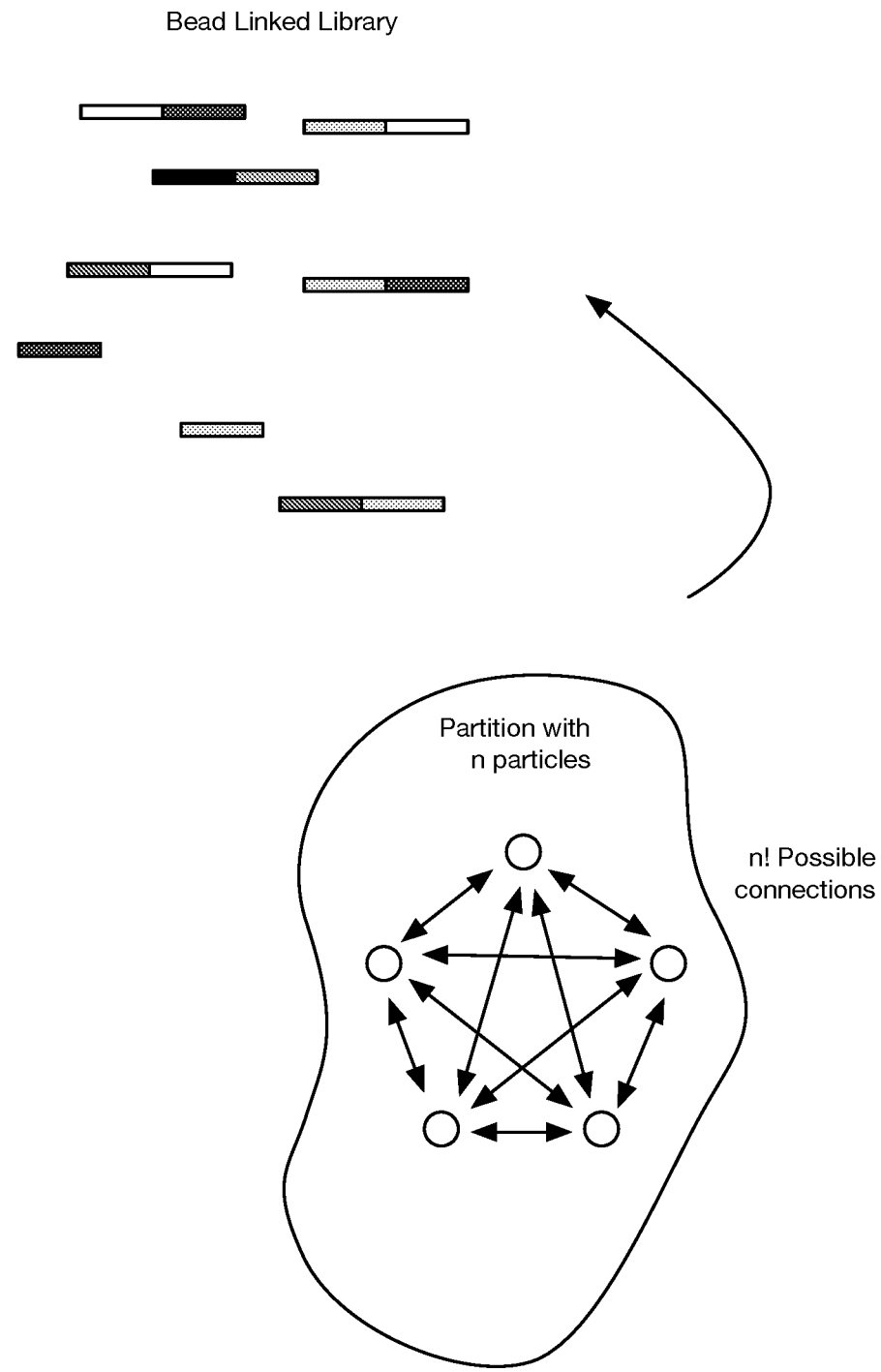

3.1.1.5 Method—Characterization of Partition Particles and Single Cell Characterization Step S460 recites: generating a network of linked barcodes from the set of amplifiable templates upon performing a set of operations. With respect to computational linkage of multiple particles to single cell material within a partition, FIG. 5D depicts a bead-linked library generated according to an embodiment of Step S440, where templates having multiple barcode sequences can be decoded by way of a set of bioinformatics processes. The number of possible connections is equal to n!, where n is the number of particles per partition. As such, the set of processes can be used to determine, for each partition, a set of particle characteristics for each partition, wherein the set of particle characteristics include a first factor describing the particles within each partition, and a second factor describing how many particles were within each partition (as in Step S470). Once the set of particle characteristics for each partition are determined, Step S480 can be implemented for generating a single cell expression library from sequenced analytes associated with the set of particle characteristics for each partition. In particular, S480 can include mapping the associated barcode sequences of a partition to sequenced single-cell targets having the same barcode sequences, and with the number of particles associated with the partition, assembling sequenced targets and generating the single cell expression library for the partition associated with the single cell (e.g., with respect to genomic expression, with respect to transcriptomics, with respect to other multi-omics, etc.).

The method 400 can, however, include other suitable steps and/or enable other downstream applications.

4. Computer Systems

Figure 6:
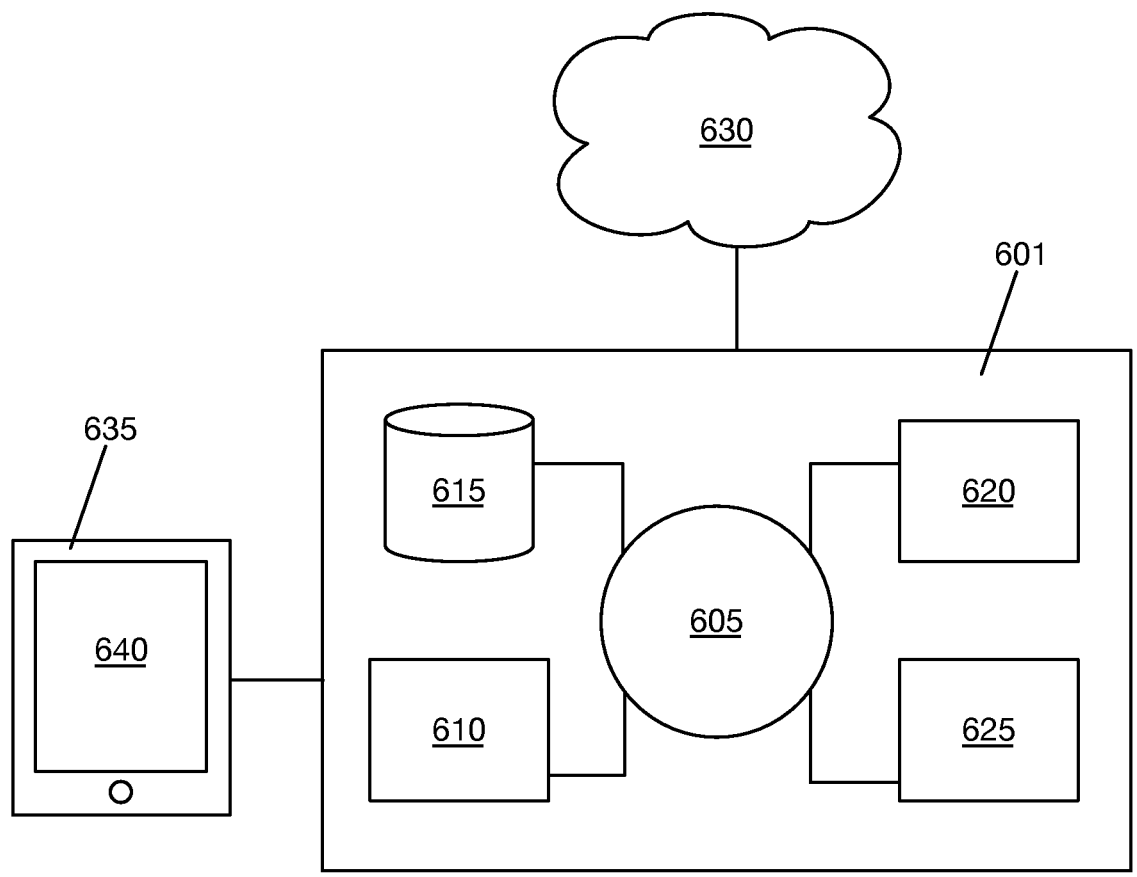
FIG. 6 illustrates a computer system that is programmed or otherwise configured to implement methods provided herein.

The present disclosure provides computer systems that are programmed to implement methods of the disclosure. FIG. 6 shows a computer system 601 that is programmed or otherwise configured to, for example, generate a plurality of droplets (e.g., from an aqueous mixture including a set of single cells and a set of functionalized particles) within a collecting container at a desired rate and with desired morphological characteristics, transmit heat to and from the plurality of droplets within the collecting container, perform an optical interrogation operation with the plurality of droplets within the collecting container, and/or performing one or more single-cell assay processes/analyses.

The computer system 601 can regulate various aspects of analysis, calculation, and generation of the present disclosure, such as, for example, generating a plurality of droplets (e.g., from an aqueous mixture including a set of single cells and a set of functionalized particles) within a collecting container at a desired rate and with desired morphological characteristics, transmitting heat to and from the plurality of droplets within the collecting container, performing an optical interrogation operation with the plurality of droplets within the collecting container, and/or performing one or more single-cell assay processes/analyses. The computer system 601 can be an electronic device of a user or a computer system that is remotely located with respect to the electronic device. The electronic device can be a mobile electronic device.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet.

In some embodiments, the network 630 is a telecommunication and/or data network. The network 630 can include one or more computer servers, which can enable distributed computing, such as cloud computing. For example, one or more computer servers may enable cloud computing over the network 630 ("the cloud") to perform various aspects of analysis, calculation, and generation of the present disclosure, such as, for example, generating a plurality of droplets within a collecting container at a predetermined rate or variation in polydispersity. Such cloud computing may be provided by cloud computing platforms such as, for example, Amazon Web Services (AWS), Microsoft Azure, Google Cloud Platform, and IBM cloud. In some embodiments, the network 630, with the aid of the computer system 601, can implement a peer-to-peer network, which may enable devices coupled to the computer system 101 to behave as a client or a server.

The CPU 605 may comprise one or more computer processors and/or one or more graphics processing units (GPUs). The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some embodiments, the circuit is an application specific integrated circuit (ASIC).

The storage unit 615 can store files, such as drivers, libraries, and saved programs. The storage unit 615 can store user data, e.g., user preferences and user programs. In some embodiments, the computer system 601 can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 1101, such as, for example, on the memory 610 or electronic storage unit 1115. The machine executable or machine readable code can be provided in the form of software. During use, the code can be executed by the processor 605. In some embodiments, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine having a processer adapted to execute the code or can be compiled during runtime. The code can be supplied in a programming language that can be selected to enable the code to execute in a pre-compiled or as-compiled fashion.

Embodiments of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, or disk drives, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for providing, for example, a visual display indicative of generating a plurality of droplets within a collecting container, transmitting heat to and from the plurality of droplets within the collecting container, performing an optical interrogation operation with the plurality of droplets within the collecting container, and/or performing one or more single-cell assay processes/analyses. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm can, for example, generate a plurality of droplets within a collecting container with desired characteristics.

5. Conclusion

The FIGURES illustrate the architecture, functionality, and operation of possible implementations of systems, methods, and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations, and equivalents. It is intended that the following claims define the scope of the invention and that methods and structures within the scope of these claims and their equivalents be covered thereby.

We claim:

1. A method comprising:
   generating a plurality of droplets within a collecting container at a rate of at least 50,000 droplets per minute, wherein the plurality of droplets is generated from an aqueous mixture comprising a set of single cells and a set of functionalized particles configured for a single cell assay;
   wherein a functionalized particle of the set of functionalized particles comprises:
      a body,
      a first subset of single cell analyte capture molecules coupled to the body,
      a second subset of releasable molecules coupled to the body, and
      a third subset of hybridization molecules coupled to the body, which hybridization molecules are configured to hybridize with nucleic acid molecules of other functionalized particles of the set of functionalized particles.

2. The method of claim 1, wherein each of a subset of the plurality of droplets comprises one single cell of the set of single cells, and a subset of functionalized particles of the set of functionalized particles.

3. The method of claim 1, wherein generating the plurality of droplets comprises driving the aqueous mixture through a substrate comprising a distribution of holes.

4. The method of claim 3, wherein driving the aqueous mixture through the substrate comprises spinning the aqueous mixture, the substrate, and a collecting container within a centrifuge, thereby driving the aqueous mixture through the substrate and into the collecting container under centrifugal force.

5. The method of claim 1, wherein generating the plurality of droplets comprises driving the aqueous mixture through a substrate comprising a distribution of holes and into an oil layer covering an aqueous layer, thereby generating an emulsion comprising the plurality of droplets, wherein droplets of the plurality of droplets are separated from each other by the aqueous layer.

6. The method of claim 1, wherein the set of single cells comprises a first number of single cells, and wherein the set of functionalized particles comprises a second number of functionalized particles, wherein the second number is greater than the first number.

7. The method of claim 1, wherein the set of single cells occupies less than 15% of the plurality of droplets.

8. The method of claim 1, wherein a percentage (p) of functionalized particles of the set of functionalized particles that are unique is greater than 99%, and wherein a percent occupancy (o) of droplets occupied by a number of single cells is less than 10% and a barcode diversity (d) is greater than five times a total number (n) of functionalized particles in the set of functionalized particles.

9. The method of claim 1, wherein a first molecule of the first subset of single cell analyte capture molecules comprises a barcode segment, a unique molecule identifier, and a capture portion.

10. The method of claim 9, wherein the capture portion is configured to bind a target messenger ribonucleic acid (mRNA).

11. The method of claim 1,
   wherein a second molecule of the second subset of releasable molecules is configured to release from the body in response to a trigger, and wherein the second molecule comprises a barcode segment and an association segment; and
   wherein a third molecule of the third subset of hybridization molecules comprises another barcode segment and a complementary association segment configured to preferentially hybridize with another association segment of another functionalized particle of the set of functionalized particles.

12. The method of claim 11, wherein the complementary association segment of the second releasable molecule does not substantially hybridize with the association segment of the third molecule.

13. The method of claim 11, wherein the trigger comprises a compound selected from the group consisting of: an enzymatic trigger, a photocleaving trigger, a pH trigger, and a heat trigger.

14. The method of claim 1, wherein the aqueous mixture further comprises a lysis reagent.

15. The method of claim 14, further comprising: transmitting heat to the collecting container, thereby lysing the set of single cells within the plurality of droplets with the lysis reagent, and wherein individual droplets of the plurality of droplets remain unmerged with adjacent droplets during lysing.

16. The method of claim 15, wherein the set of functionalized particles is configured to capture target nucleic acid molecules from lysed cells of the set of single cells.

17. A method comprising:
   generating a plurality of droplets within a collecting container at a rate of at least 20,000 droplets per minute under centrifugal force, wherein the plurality of droplets is generated from an aqueous mixture comprising a set of single cells and a set of functionalized particles configured for a single cell assay, and wherein the set of single cells comprises a first number of single cells which is less than a second number of functionalized particles of the set of functionalized particles;
   permitting hybridization between complementary regions of molecules of a subset of functionalized particles of the set of functionalized particles within a droplet of the plurality of droplets, thereby co-associating the subset of functionalized particles within the droplet; and
   capturing a target of a single cell co-localized with the subset of functionalized particles within the droplet.

18. The method of claim 17, wherein the aqueous mixture further comprises a lysis reagent, the method further comprising: transmitting heat to the collecting container, thereby lysing the set of single cells within the plurality of droplets with the lysis reagent, and wherein individual droplets of the plurality of droplets remain unmerged with adjacent droplets during lysing.

19. The method of claim 17, wherein generating the plurality of droplets comprises driving the aqueous mixture under the centrifugal force through a substrate comprising a distribution of holes.

20. The method of claim 17, wherein the set of functionalized particles is configured to bind to a target messenger ribonucleic acid (mRNA).

21. The method of claim 18, wherein the set of functionalized particles is configured for target nucleic acid capture from lysed cells of the set of single cells.

\* \* \* \* \*